United States Patent
Inaba et al.

(10) Patent No.: US 11,253,834 B2
(45) Date of Patent: Feb. 22, 2022

(54) FLOW REACTION FACILITY AND FLOW REACTION METHOD

(71) Applicant: FUJIFILM Corporation, Tokyo (JP)

(72) Inventors: Tatsuya Inaba, Kanagawa (JP); Masataka Hasegawa, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 0 days.

(21) Appl. No.: 17/173,599

(22) Filed: Feb. 11, 2021

(65) Prior Publication Data

US 2021/0162363 A1 Jun. 3, 2021

Related U.S. Application Data

(63) Continuation of application No. PCT/JP2019/030922, filed on Aug. 6, 2019.

(30) Foreign Application Priority Data

Sep. 28, 2018 (JP) .............................. JP2018-185156

(51) Int. Cl.
 *B01J 19/00* (2006.01)
 *B01J 19/18* (2006.01)
(52) U.S. Cl.
 CPC ........... *B01J 19/0033* (2013.01); *B01J 19/18* (2013.01); *B01J 2219/00243* (2013.01)
(58) Field of Classification Search
 CPC ........ B01J 19/0033; B01J 19/24; B01J 19/18; B01J 2219/002; B01J 2219/00229; B01J 2219/00234; B01J 2219/00243
 See application file for complete search history.

(56) References Cited

U.S. PATENT DOCUMENTS

| 4,754,410 | A | 6/1988 | Leech et al. |
|---|---|---|---|
| 5,362,917 | A | 11/1994 | Ogawa et al. |
| 8,986,618 | B2 | 3/2015 | Dudish et al. |
| 2007/0260357 | A1 | 11/2007 | Issberner et al. |
| 2010/0145896 | A1 | 6/2010 | Yuta |

(Continued)

FOREIGN PATENT DOCUMENTS

| JP | S62-249203 A | 10/1987 |
|---|---|---|
| JP | H05-140230 A | 6/1993 |

(Continued)

OTHER PUBLICATIONS

International Search Report issued in PCT/JP2019/030922; dated Nov. 5, 2019.

(Continued)

*Primary Examiner* — Lessanework Seifu
(74) *Attorney, Agent, or Firm* — Studebaker & Brackett PC

(57) ABSTRACT

A flow reaction facility 10 includes a reaction section 23, a collecting section 26, a system controller 15, a first flow velocimeter to a third flow velocimeter 35a to 35c, a thermometer 35d, and a soft sensor 38. The first flow velocimeter to the third flow velocimeter 35a to 35c and the thermometer 35d detect reaction conditions in the reaction section 23, and output the detected reaction conditions as detection information. The soft sensor 38 applies the above detection information to a prediction function generated in advance using measurement data, and calculates a reaction result in the reaction section 23 as an arithmetic reaction result. The system controller 15 controls the reaction section 23 on the basis of the arithmetic reaction result.

20 Claims, 12 Drawing Sheets

(56) References Cited

U.S. PATENT DOCUMENTS

| | | |
|---|---|---|
| 2010/0209307 A1 | 8/2010 | Drabish et al. |
| 2015/0133306 A1 | 5/2015 | Cronin |
| 2015/0148514 A1 | 5/2015 | Makal et al. |

FOREIGN PATENT DOCUMENTS

| | | |
|---|---|---|
| JP | H06-28009 A | 2/1994 |
| JP | H06-199904 A | 7/1994 |
| JP | H07-82203 A | 3/1995 |
| JP | 2001-356803 A | 12/2001 |
| JP | 2002-301359 A | 10/2002 |
| JP | 2008-501837 A | 1/2008 |
| JP | 2015-520674 A | 7/2015 |
| WO | 2009/025045 A1 | 2/2009 |

OTHER PUBLICATIONS

International Preliminary Report On Patentability and Written Opinion issued in PCT/JP2019/030922; dated Mar. 23, 2021.
The extended European search report issued by the European Patent Office dated Nov. 18, 2021, which corresponds to European Patent Application No. 17173599.6-1104 and is related to U.S. Appl. No. 17/173,599.

FIG. 4

| REACTION INFORMATION | REACTION CONDITION ||||||| REACTION RESULT ||
|---|---|---|---|---|---|---|---|---|---|
| | FIRST RAW MATERIAL || SECOND RAW MATERIAL || MERGING SECTION | REACTION SECTION || REACTION TEMPERATURE | PRODUCT ||
| | CONCENTRATION | FLOW VELOCITY | CONCENTRATION | FLOW VELOCITY | SHAPE | REACTION PATH DIAMETER | REACTION PATH LENGTH | | DISPERSITY | MOLECULAR WEIGHT |
| | (mol/l) | (ml/min) | (mol/l) | (ml/min) | | (mm) | (m) | (°C) | | |
| a | 0.018 | 10 | 0.018 | 5.5 | T-SHAPE | 1 | 8 | 0 | 1.0422 | 27000 |
| b | 0.018 | 20 | 0.018 | 11 | T-SHAPE | 1 | 8 | 10 | 1.1334 | 21340 |
| c | 0.018 | 100 | 0.018 | 55 | T-SHAPE | 10 | 8 | 10 | 1.0575 | 22000 |
| d | 0.018 | 11 | 0.018 | 5.6 | T-SHAPE | 5 | 8 | 10 | 1.0560 | 25200 |
| e | 0.018 | 20 | 0.018 | 11 | T-SHAPE | 5 | 8 | 10 | 1.0631 | 28300 |
| f | 0.018 | 20 | 0.018 | 11 | T-SHAPE | 1 | 8 | 10 | 1.0655 | 18000 |
| g | 0.018 | 20 | 0.018 | 20 | CROSS-SHAPE | 2 | 8 | 0 | 1.1164 | 22300 |
| h | 0.018 | 20 | 0.018 | 20 | T-SHAPE | 2 | 8 | 0 | 1.2328 | 14900 |
| i | 0.018 | 20 | 0.018 | 20 | T-SHAPE | 4 | 8 | 0 | 1.0845 | 23500 |
| j | 0.018 | 1 | 0.018 | 0.6 | T-SHAPE | 1 | 8 | 0 | 1.0431 | 11560 |

FIG. 5

| REACTION CONDITION ||||||||
|---|---|---|---|---|---|---|---|
| FIRST RAW MATERIAL || SECOND RAW MATERIAL || MERGING SECTION | REACTION SECTION || |
| CONCENTRATION | FLOW VELOCITY | CONCENTRATION | FLOW VELOCITY | SHAPE | REACTION PATH DIAMETER | REACTION PATH LENGTH | REACTION TEMPERATURE |
| (mol/l) | (ml/min) | (mol/l) | (ml/min) | | (mm) | (m) | (°C) |
| 0.018 | 1 | 0.018 | 0.6 | T-SHAPE | 1 | 8 | 0 |
| 0.018 | 2 | 0.018 | 0.6 | T-SHAPE | 1 | 8 | 0 |
| 0.018 | 3 | 0.018 | 0.6 | T-SHAPE | 1 | 8 | 0 |
| ... | ... | ... | ... | ... | ... | ... | ... |
| 0.018 | 100 | 0.018 | 0.6 | T-SHAPE | 1 | 8 | 0 |
| 0.018 | 1 | 0.018 | 0.7 | T-SHAPE | 1 | 8 | 0 |
| 0.018 | 1 | 0.018 | 0.8 | T-SHAPE | 1 | 8 | 0 |
| ... | ... | ... | ... | ... | ... | ... | ... |
| 0.018 | 1 | 0.018 | 55.0 | T-SHAPE | 1 | 8 | 0 |
| 0.018 | 1 | 0.018 | 0.6 | CROSS-SHAPE | 1 | 8 | 0 |
| 0.018 | 2 | 0.018 | 0.6 | CROSS-SHAPE | 1 | 8 | 0 |
| 0.018 | 3 | 0.018 | 0.6 | CROSS-SHAPE | 1 | 8 | 0 |
| ... | ... | ... | ... | ... | | | |

FIG. 6

| REACTION INFORMATION No. | REACTION CONDITION ||||||||| REACTION RESULT ||
| --- | --- | --- | --- | --- | --- | --- | --- | --- | --- | --- |
| | FIRST RAW MATERIAL || SECOND RAW MATERIAL || MERGING SECTION | REACTION SECTION || REACTION TEMPERATURE | PRODUCT ||
| | CONCENTRATION | FLOW VELOCITY | CONCENTRATION | FLOW VELOCITY | SHAPE | REACTION PATH DIAMETER | REACTION PATH LENGTH | | DISPERSITY | MOLECULAR WEIGHT |
| | (mol/l) | (ml/min) | (mol/l) | (ml/min) | | (mm) | (m) | (°C) | | |
| 1 | 0.018 | 1 | 0.018 | 0.6 | T-SHAPE | 1 | 8 | 0 | 1.07453 | 29876 |
| 2 | 0.018 | 2 | 0.018 | 0.6 | T-SHAPE | 1 | 8 | 0 | 1.07488 | 29654 |
| 3 | 0.018 | 3 | 0.018 | 0.6 | T-SHAPE | 1 | 8 | 0 | 1.07323 | 29403 |
| ... | ... | ... | ... | ... | ... | ... | ... | ... | ... | ... |
| 100 | 0.018 | 100 | 0.018 | 0.6 | T-SHAPE | 1 | 8 | 0 | 1.09234 | 29560 |
| 101 | 0.018 | 1 | 0.018 | 0.7 | T-SHAPE | 1 | 8 | 0 | 1.06832 | 28338 |
| 102 | 0.018 | 1 | 0.018 | 0.8 | T-SHAPE | 1 | 8 | 0 | 1.06555 | 28762 |
| ... | ... | ... | ... | ... | ... | ... | ... | ... | ... | ... |
| | 0.018 | 3 | 0.018 | 10.2 | CROSS-SHAPE | 2 | 8 | 0 | 1.05743 | 27835 |
| | 0.018 | 3 | 0.018 | 10.3 | CROSS-SHAPE | 2 | 8 | 0 | 1.05464 | 27856 |
| | 0.018 | 3 | 0.018 | 10.4 | CROSS-SHAPE | 2 | 8 | 0 | 1.05382 | 27832 |
| ... | ... | ... | ... | ... | ... | ... | ... | ... | ... | ... |
| 6050 * | 0.018 | 8 | 0.018 | 3.2 | T-SHAPE | 6 | 8 | 0 | 1.0389 | 24870 |
| ... | ... | ... | ... | ... | ... | ... | ... | ... | ... | ... |
| 8000 | 0.018 | 10 | 0.018 | 3.2 | T-SHAPE | 6 | 8 | 0 | 1.05702 | 24870 |
| ... | ... | ... | ... | ... | ... | ... | ... | ... | ... | ... |

FIG.7

| | REACTION CONDITION | | | | | | | | REACTION RESULT | | |
|---|---|---|---|---|---|---|---|---|---|---|---|
| | FIRST RAW MATERIAL | | SECOND RAW MATERIAL | | MERGING SECTION | REACTION SECTION | | REACTION TEMPERATURE | PRODUCT | | |
| | CONCENTRATION (mol/l) | FLOW VELOCITY (ml/min) | CONCENTRATION (mol/l) | FLOW VELOCITY (ml/min) | SHAPE | REACTION PATH DIAMETER (mm) | REACTION PATH LENGTH (m) | (°C) | DISPERSITY | MOLECULAR WEIGHT | |
| PREDICTION RESULT RP | 0.018 | 8 | 0.018 | 3.2 | T-SHAPE | 6 | 8 | 0 | 1.0389 | 24870 | → DIFFERENCE DR = 3.5107 |
| MEASUREMENT RESULT RR | 0.018 | 8 | 0.018 | 3.2 | T-SHAPE | 6 | 8 | 0 | 1.0767 | 27630 | → DIFFERENCE DR = 9.9891 |

FIG. 9

| REACTION INFORMATION | REACTION CONDITION ||||||||| REACTION RESULT ||
| | FIRST RAW MATERIAL || SECOND RAW MATERIAL || MERGING SECTION | REACTION SECTION || REACTION TEMPERATURE | PRODUCT ||
| | CONCENTRATION (mol/l) | FLOW VELOCITY (ml/min) | CONCENTRATION (mol/l) | FLOW VELOCITY (ml/min) | SHAPE | REACTION PATH DIAMETER (mm) | REACTION PATH LENGTH (m) | (°C) | DISPERSITY | MOLECULAR WEIGHT |
|---|---|---|---|---|---|---|---|---|---|---|
| a | 0.018 | 10 | 0.018 | 5.5 | T-SHAPE | 1 | 8 | 0 | 1.0422 | 27000 |
| b | 0.018 | 20 | 0.018 | 11 | T-SHAPE | 1 | 8 | 10 | 1.1334 | 21340 |
| c | 0.018 | 100 | 0.018 | 55 | T-SHAPE | 10 | 8 | 10 | 1.0575 | 22000 |
| d | 0.018 | 11 | 0.018 | 5.6 | T-SHAPE | 5 | 8 | 10 | 1.0560 | 25200 |
| e | 0.018 | 20 | 0.018 | 11 | T-SHAPE | 5 | 8 | 10 | 1.0631 | 28300 |
| f | 0.018 | 20 | 0.018 | 11 | T-SHAPE | 1 | 8 | 10 | 1.0655 | 18000 |
| g | 0.018 | 20 | 0.018 | 20 | CROSS-SHAPE | 2 | 8 | 0 | 1.1164 | 22300 |
| h | 0.018 | 20 | 0.018 | 20 | T-SHAPE | 2 | 8 | 0 | 1.2328 | 14900 |
| i | 0.018 | 20 | 0.018 | 20 | T-SHAPE | 4 | 8 | 0 | 1.0845 | 23500 |
| j | 0.018 | 1 | 0.018 | 0.6 | T-SHAPE | 1 | 8 | 0 | 1.0431 | 11560 |
| k | 0.018 | 37 | 0.018 | 14.9 | T-SHAPE | 3 | 8 | 0 | 1.0767 | 27630 |

FIG. 10

| | REACTION CONDITION | | | | | | | | REACTION RESULT | |
|---|---|---|---|---|---|---|---|---|---|---|
| | FIRST RAW MATERIAL | | SECOND RAW MATERIAL | | MERGING SECTION | REACTION SECTION | | REACTION TEMPERATURE | PRODUCT | |
| | CONCENTRATION (mol/l) | FLOW VELOCITY (ml/min) | CONCENTRATION (mol/l) | FLOW VELOCITY (ml/min) | SHAPE | REACTION PATH DIAMETER (mm) | REACTION PATH LENGTH (m) | (°C) | DISPERSITY | MOLECULAR WEIGHT |
| PREDICTION RESULT RP | 0.018 | 37 | 0.018 | 14.9 | T-SHAPE | 3 | 8 | | 1.0474 | 27350 |
| MEASUREMENT RESULT RR | 0.018 | 37 | 0.018 | 14.9 | T-SHAPE | 3 | 8 | | 1.0721 | 25730 |

→ DIFFERENCE DR = 2.3039
→ DIFFERENCE DR = 6.2962

FIG. 11

| | REACTION CONDITION | | | | | | | | REACTION RESULT | |
|---|---|---|---|---|---|---|---|---|---|---|
| | FIRST RAW MATERIAL | | SECOND RAW MATERIAL | | MERGING SECTION | REACTION SECTION | | REACTION TEMPERATURE | PRODUCT | |
| | CONCENTRATION | FLOW VELOCITY | CONCENTRATION | FLOW VELOCITY | SHAPE | REACTION PATH DIAMETER | REACTION PATH LENGTH | | DISPERSITY | MOLECULAR WEIGHT |
| | (mol/l) | (ml/min) | (mol/l) | (ml/min) | | (mm) | (m) | (°C) | | |
| PREDICTION RESULT RP | 0.018 | 40 | 0.018 | 19.1 | T-SHAPE | 2 | 8 | 0 | 1.0321 | 25320 |
| MEASUREMENT RESULT RR | 0.018 | 40 | 0.018 | 19.1 | T-SHAPE | 2 | 8 | 0 | 1.0342 | 25210 |

DIFFERENCE DR = 0.2031

DIFFERENCE DR = 0.4363

FLOW REACTION FACILITY AND FLOW REACTION METHOD

CROSS-REFERENCE TO RELATED APPLICATIONS

This application is a Continuation of PCT International Application No. PCT/JP2019/030922 filed on Aug. 6, 2019, which claims priority under 35 U.S.C § 119(a) to Japanese Patent Application No. 2018-185156 filed on Sep. 28, 2018. Each of the above application(s) is hereby expressly incorporated by reference, in its entirety, into the present application.

BACKGROUND OF THE INVENTION

1. Field of the Invention

The present invention relates to a flow reaction facility and a flow reaction method.

2. Description of the Related Art

Methods for causing a reaction of a raw material containing a reactant include a so-called batch method for causing the reaction of the raw material in a state of being accommodated in a container, and a continuous method for causing the reaction of the raw material during flow. The continuous reaction is called a flow reaction since the reaction is performed while the raw material is flowing.

In a flow reaction process, since the reaction is continuously carried out, a product can be easily obtained with uniform properties. Further, the flow reaction process has an advantage that the productivity is higher than that of the batch method.

In this regard, there is a technique of utilizing various computations using, for example, a neural network for a chemical reaction process. For example, in Japanese Unexamined Patent Publication No. 2002-301359, data under abnormal conditions of each measurement device of a chemical reactor is computed by a neural network that is learned and stored in advance in a program. Further, in a case where the calculation value deviates from a set normal allowable band value, an abnormal signal is output to a neuro controller, and a correction control signal is sent to each part of the chemical reactor, to thereby control the abnormal reaction. Thus, the abnormal state of the chemical reactor is immediately detected, and a quick and accurate control is performed.

WO2009/025045A discloses, as a method of predicting physical properties of a compound, a technique of applying a created prediction model to an unknown sample to calculate prediction items. In this technique, the degree of similarity between the unknown sample and an individual learning sample is calculated on the basis of a plurality of parameter values acquired for the unknown sample and the individual learning sample, and learning samples having the degree of similarity equal to or higher than a preset threshold value are extracted to form a sub-sample set. Then, data analysis of the sub-sample set is performed to create a prediction model, and this prediction model is applied to the unknown sample to calculate prediction items.

Further, JP2015-520674A discloses a technique for controlling a flow reaction using a genetic algorithm to thereby produce a target product.

SUMMARY OF THE INVENTION

For example, due to a disturbance such as a sudden change in temperature, reaction conditions may change during a reaction process, and thus, a target product may not be obtained. In a case where the reaction conditions change, in a batch type reaction process, even in a case where its lot is discarded, only the loss for the lot occurs, but in a flow reaction process, the amount to be discarded is much larger than that in the batch method. Further, since the flow reaction process has condition parameters unique to the flow reaction such as a flow rate, the reaction conditions are likely to change with a higher probability than the batch type reaction.

Accordingly, an object of the present disclosure is to provide a flow reaction facility and a flow reaction method capable of reducing a disposal volume even in a case where reaction conditions change during a reaction process.

According to an aspect of the present disclosure, there is provided a flow reaction facility that comprises a reaction section, a collecting section, a system controller, a sensor, and a prediction computing section. The reaction section causes a reaction of a raw material during flow. The collecting section collects a product. The system controller controls the reaction section under a set reaction condition. The sensor detects the reaction condition in the reaction section and outputs the detected reaction condition as detection information. The prediction computing section applies the detection information from the sensor to a prediction function that is generated in advance using measurement data including a plurality of pieces of reaction information in which a reaction condition whose reaction result is known and the reaction result are associated with each other and calculates a reaction result in the reaction section as an arithmetic reaction result. The system controller controls the reaction section on the basis of the arithmetic reaction result.

It is preferable that the sensor detects the reaction condition at a regular time interval.

It is preferable that the flow reaction facility further comprises a computing section and a determination section. The computing section calculates a prediction result for each reaction condition of a condition data set having a plurality of reaction conditions whose reaction results are unknown using a function generated from the measurement data to generate a prediction data set in which the reaction condition and the prediction result are associated with each other, specifies the prediction result closest to a preset target result among a plurality of the obtained prediction results, and extracts a reaction condition associated with the specified prediction result as an extracted reaction condition. The determination section determines whether or not a difference between the reaction result in a case where the reaction is performed under the extracted reaction condition and the prediction result associated with the extracted reaction condition is within a preset allowable range, adds reaction information in which the extracted reaction condition and the reaction result in a case where the reaction is performed under the extracted reaction condition are associated with each other to the measurement data in a case where the difference is not within the allowable range, and sets the extracted reaction condition as a reaction condition to be used in a flow reaction process in a case where the difference is within the allowable range. The prediction computing section uses the function used by the computing section as the prediction function in a case where the determination section determines that the difference is within the allowable range.

It is preferable that the reaction condition is any one of a flow rate of the raw material, a flow velocity of the raw material, a concentration of a reactant in the raw material, a temperature of the raw material, a set temperature of the reaction, or a reaction time.

It is preferable that the reaction result is any one of a yield of a product, a yield of a by-product, a molecular weight of the product, a molecular weight dispersity of the product, or a molar concentration of the product.

According to another aspect of the present disclosure, there is provided a flow reaction method includes a flow reaction step, a collecting step, a sensing step, and a prediction computing step. The flow reaction step is performed to control, using a system controller that controls a reaction section that causes a reaction of a raw material during flow, the reaction section under a set reaction condition to cause the reaction of the raw material. The collecting step is performed to collect a product generated by the reaction. The sensing step is performed to detect a reaction condition during the flow reaction step. The prediction computing step is performed to apply detection information obtained in the sensing step to a prediction function that is generated in advance using measurement data including a plurality of pieces of reaction information in which a reaction condition whose reaction result is known and the reaction result are associated with each other and calculates a reaction result in the reaction section as an arithmetic reaction result. The system controller controls the reaction section on the basis of the arithmetic reaction result.

It is preferable that the sensing step includes detecting the reaction condition at a regular time interval.

It is preferable that the flow reaction method further includes a learning and computing step and a determination step. The learning and computing step is performed to calculate a prediction result for each reaction condition of a condition data set having a plurality of reaction conditions whose reaction results are unknown using a function generated from the measurement data to generate a prediction data set in which the reaction condition and the prediction result are associated with each other, specifying the prediction result closest to a preset target result among a plurality of the obtained prediction results, and extracting a reaction condition associated with the specified prediction result as an extracted reaction condition. The determination step is performed to determine whether or not a difference between the reaction result in a case where the reaction is performed under the extracted reaction condition and the prediction result associated with the extracted reaction condition is within a preset allowable range, adding reaction information in which the extracted reaction condition and the reaction result in a case where the reaction is performed under the extracted reaction condition are associated with each other to the measurement data in a case where the difference is not within the allowable range, and adding the extracted reaction condition to a reaction condition to be used in a flow reaction process in a case where the difference is within the allowable range. The learning and computing step and the determination step are newly repeated in a case where the reaction information is added to the measurement data in the determination step, and in the prediction computing step, the function used by the computing section is used as the prediction function in a case where the determination section determines that the difference is within the allowable range.

It is preferable that the reaction condition is any one of a flow rate of the raw material, a flow velocity of the raw material, a concentration of a reactant in the raw material, a temperature of the raw material, a set temperature of the reaction, or a reaction time.

It is preferable that the reaction result is any one of a yield of a product, a yield of a by-product, a molecular weight of the product, a molecular weight dispersity of the product, or a molar concentration of the product.

According to the present disclosure, it is possible to reduce a disposal volume even in a case where the reaction conditions change during the reaction process.

BRIEF DESCRIPTION OF THE DRAWINGS

FIG. 4 is a diagram illustrating the first measurement data.

FIG. 5 is a diagram illustrating the first condition data set.

FIG. 6 is a diagram illustrating the first prediction data set.

FIG. 7 is a diagram illustrating the first comparison data.

FIG. 9 is a diagram illustrating the second measurement data.

FIG. 10 is a diagram illustrating the second comparison data.

FIG. 11 is a diagram illustrating the seventh comparison data.

DESCRIPTION OF THE PREFERRED EMBODIMENTS

Figure 1:
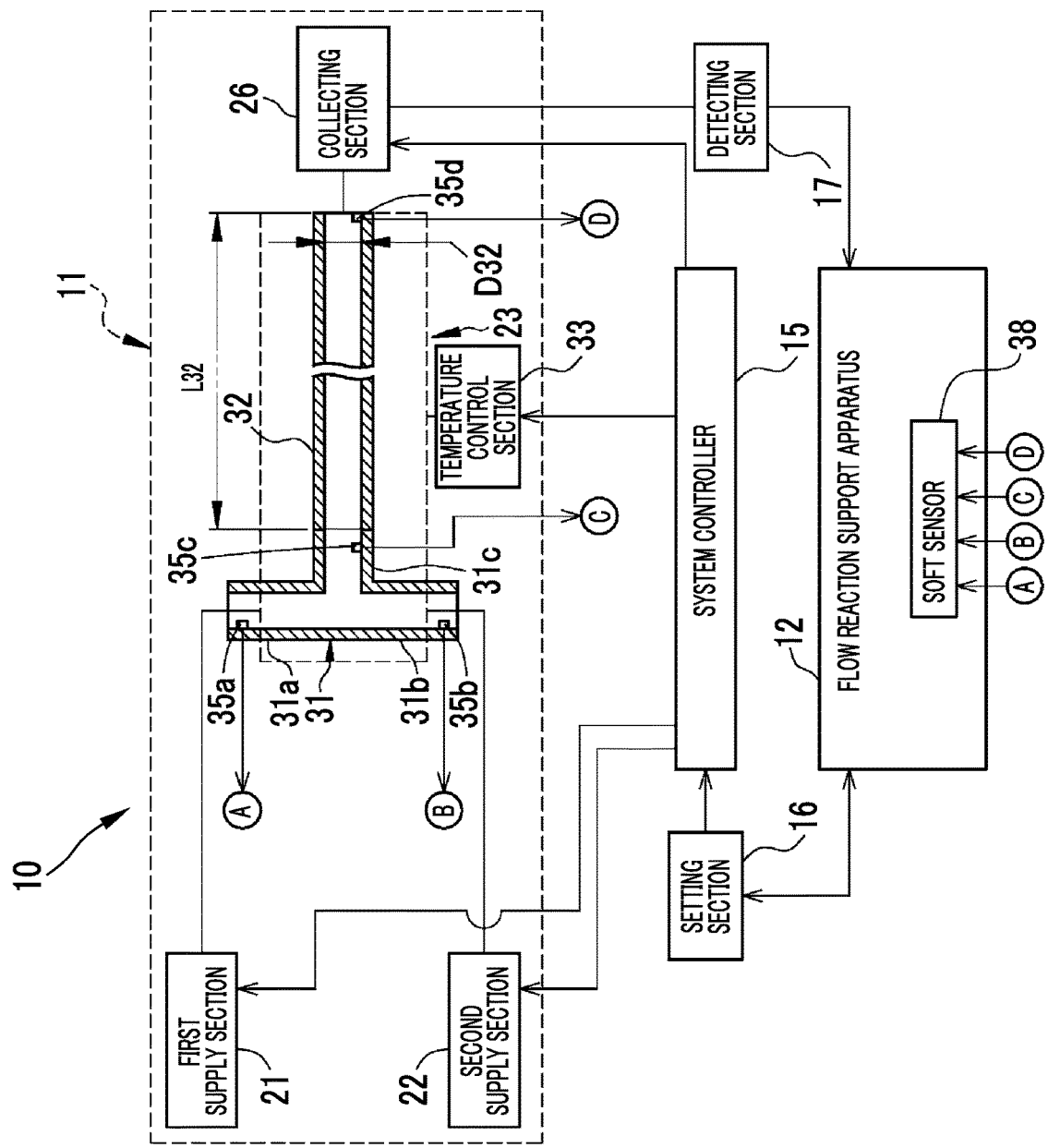
FIG. 1 is a schematic diagram showing a flow reaction facility.

As shown in FIG. 1, a flow reaction facility 10 according to an embodiment of the present invention comprises a flow reactor 11, a flow reaction support apparatus (hereinafter, simply referred to as a "support apparatus") 12, a system controller 15, a setting section 16, a detecting section 17, and the like. The flow reactor 11 is an apparatus that performs a flow reaction process to obtain a product.

The flow reaction performed in the flow reactor 11 may be, for example, a synthesis reaction for synthesizing a compound that is a monomer, or a polymerization reaction for producing a polymer by causing a reaction of monomers, or may be elementary reactions such as an initiation and a termination reaction in an anionic polymerization reaction, for example. Accordingly, a reactant that is a target of the flow reaction may be, for example, a vegetation (growth) stage compound that is a target of the termination reaction. In this example, the termination reaction of stopping the vegetation (growth) of polystyryllithium with methanol is performed by the flow reaction.

The flow reactor 11 comprises a first supply section 21, a second supply section 22, a reaction section 23, and a collecting section 26. The first supply section 21 and the second supply section 22 are respectively connected to upstream end parts of the reaction section 23 by piping, and the collecting section 26 is connected to a downstream end part of the reaction section 23 by piping.

The first supply section 21 is a member for supplying a first raw material of the flow reaction to the reaction section 23. The first raw material in this example is a first liquid obtained by dissolving polystyryllithium in a solvent, and polystyryllithium is an example of a reactant of the flow reaction process. In this example, the first supply section 21 supplies the first liquid obtained by dissolving polystyryllithium in the solvent to the reaction section 23. Tetrahydrofuran (hereinafter, referred to as THF) is used as the solvent, and a small amount of toluene and hexane are mixed in the first solution. In this way, the raw material of the flow reaction may be a mixture of the reactant and another substance, or may be formed of only the reactant. The first supply section 21 comprises a pump (not shown), and a flow rate of the first raw material to the reaction section 23 is controlled by controlling a rotating speed of the pump.

The second supply section 22 is a member for supplying a second raw material of the flow reaction to the reaction section 23. The second raw material in this example is a mixture of methanol and water, that is, an aqueous methanol solution, and methanol is used as a terminating agent for the termination reaction. The second supply section 22 also comprises a pump (not shown) like the first supply section 21, and a flow rate of methanol to the reaction section 23 is controlled by controlling a rotating speed of the pump. In the present example, the first supply section 21 and the second supply section 22 supply a liquid to the reaction section 23, but the supply is not limited to the liquid and may be a solid or a gas.

The reaction section 23 is a member for performing a termination reaction as a flow reaction, and comprises a merging section 31, a reaction section 32, and a temperature control section 33. The merging section 31 is a tube having T-shaped branches, that is, a T-shaped tube. A first tube part 31a of the merging section 31 is connected to the first supply section 21, a second tube part 31b thereof is connected to the second supply section 22, and a third tube part 31c thereof is connected to the reaction section 32. Thus, the guided first raw material and second raw material merge with each other and are sent to the reaction section 32 in a mixed state.

The reaction section 32 is a tube in which a plurality of tubular members are connected in the length direction. A length L32 of the reaction section 32 is changed by changing the number of tubular members and/or the length of each tubular member that is used. Further, an inner diameter D32 of the reaction section 32 is changed by changing the tubular members to other tubular members having a different inner diameter.

The inside of the reaction section 32 is a flow path for a mixture (hereinafter, referred to as a mixed raw material) of the first raw material and the second raw material, and a hollow portion in the tube is defined as a reaction site. The mixed raw material undergoes an anionic polymerization termination reaction while passing through the reaction section 32, so that polystyrene is produced. The reaction also proceeds slightly in the third tube part 31c of the merging section 31, but the length of the third tube part 31c of the merging section 31 is very short with respect to the length L32 (in this example, 8 m) of the reaction section 32, which is approximately 0.03 m in this example. Accordingly, the length of the third tube part 31c is ignored, and the length L32 of the reaction section 32 is regarded as the length of a site where the flow reaction is performed (hereinafter, referred to as a reaction path length). Hereinafter, the reference numeral L32 is used for the reaction path length. Similarly, the inner diameter D32 of the reaction section 32 is regarded as the diameter of the site where the flow reaction is performed (hereinafter, referred to as a reaction path diameter), and the reference numeral D32 is used for the reaction path diameter.

The temperature control section 33 is a member for controlling a temperature of the flow reaction (hereinafter, referred to as a reaction temperature). The temperature control section 33 controls the temperature (reaction temperature) of the mixed raw material flowing in and through the merging section 31 and the reaction section 32.

The flow reactor 11 further comprises one sensor or a plurality of sensors. For example, in this example, four sensors, that is, a first sensor to a fourth sensor are provided. The first sensor is a first flow velocimeter 35a, the second sensor is a second flow velocimeter 35b, the third sensor is a third flow velocimeter 35c, and the fourth sensor is a thermometer 35d, which form a sensor section 36 (see FIG. 3). In the following description, in a case where the first flow velocimeter 35a, the second flow velocimeter 35b, the third flow velocimeter 35c, and the thermometer 35d are not distinguished, they are referred to as sensors 35. Each sensor 35 performs the following detection during a flow reaction in an operation mode to be described later.

The first flow velocimeter 35a is provided at an inlet of a first tube part 31a, detects a flow velocity of a first raw material, and outputs the result to a soft sensor 38 of the flow reaction support apparatus 12 as a detection signal. The second flow velocimeter 35b is provided at an inlet of a second tube part 31b, detects a flow velocity of a second raw material, and outputs the result to the soft sensor 38 as a detection signal. The third flow velocimeter 35c is provided at an inlet of the reaction section 32, detects a flow velocity of a mixed raw material, and outputs the result to the soft sensor 38 as a detection signal. The thermometer 35d is provided inside a downstream end of the reaction section 32, detects a reaction temperature, and outputs the result to the soft sensor 38 as a detection signal.

The sensors 35 respectively perform the above detections at a regular time interval. The detection time interval is preferably in a range of 1 second or more and 60 seconds or less, and in this example, the detection is performed at an interval of 1 second.

The collecting section 26 is a product for collecting polystyrene that is a product of the flow reaction. The collecting section 26 includes a precipitating part (not shown), a sampling part (not shown), a drying part (not shown), a disposal part (not shown), and the like. The precipitating part, the sampling part, and the drying part are connected in series in this order, and function as a first collecting section for collecting an obtained product. The disposal part is connected in parallel with the precipitating part, and functions as a second collecting section for collecting unnecessary disposal targets. A switching valve (not shown) is provided at a branching portion between the disposal part and the precipitating part, and using the switching valve, a liquid guided from the reaction section 23 is divided into the first collecting section or the second collecting section as any one of the product or the disposal targets.

The precipitating part is a member for precipitating the produced polystyrene. In this example, a container equipped with a stirrer is used as the precipitating part. In a state where methanol is accommodated and stirred in a container, and polystyrene is precipitated by putting a polystyrene solution guided from the reaction section into the methanol.

The sampling part is a member for sampling the precipitated polystyrene from a mixed solution of methanol, THF, and the like. In this example, a filter is used as the sampling part.

The drying part is a member for drying the sampled polystyrene. In this example, a thermostatic chamber having a pressure reducing function is used as the drying part. Polystyrene may be obtained by heating the inside of the thermostatic chamber in a decompressed state.

The disposal part is a tank in this example. The disposal part stores the guided liquid as a disposal target.

The reaction section and the collecting section are not limited to the above examples, and may be appropriately changed depending on the type of the flow reaction and/or the type of the product. For example, a container may be provided instead of the collecting section 26, and the polystyrene solution guided from the reaction section 23 may be temporarily stored in this container. In this case, for example, the stored polystyrene solution is guided to the collecting section 26, and the product may be obtained by precipitating, sampling, and drying the polystyrene.

The detecting section 17 is connected to the first collecting section of the collecting section 26 and the support apparatus 12, detects a reaction result that is a processing result of the flow reaction, and outputs the result to the determination section 56 (see FIG. 3A) of the support apparatus 12. Examples of parameters that correspond to the reaction result (hereinafter, referred to as "result parameters") include properties and states of a product such as a purity, a molecular weight, or a molecular weight dispersity (hereinafter, simply referred to as a dispersity) of the product, a yield of the product, and the like. In addition, in a case where the product is obtained in the collecting section 26 in a solution state in which the product is dissolved in a solvent, for example, the concentration of the product in the solution (molar concentration or the like) may be detected as a result parameter. In addition to the various properties and states of the product and the yield thereof, the detecting section 17 may detect a yield or various properties and states such as a purity of a by-product as result parameters. A plurality of result parameters may form the reaction result.

In this example, the detecting section 17 detects the molecular weight and the dispersity of polystyrene obtained in the first collecting section of the collecting section 26. That is, the result parameters in this example are two parameters of the molecular weight and the dispersity. The detected molecular weight is a number-average molecular weight (Mn). The molecular weight and the dispersity are determined by dissolving polystyrene in THF to prepare a polystyrene solution and using this polystyrene solution by gel permeation chromatography (hereinafter, referred to as GPC (GPC is an abbreviation for Gel Permeation Chromatography)). The dispersity is Mw/Mn obtained by dividing a weight average molecular weight (Mw) by the number-average molecular weight. The detection of the result parameters is not limited to GPC. For example, the detection of the result parameters may be performed by various methods such as infrared spectroscopy (IR), nuclear magnetic resonance spectroscopy (NMR), high performance liquid chromatography (HPLC), or gas chromatography (GC).

GPC is measured under the following conditions.
Apparatus: HLC-8220GPC (manufactured by Tosoh Corp.)
Detector: Differential refractometer (Refractive Index (RI) detector)
Pre-column: TSKGUARDCOLUMN HXL-L 6 mm×40 mm (manufactured by Tosoh Corp.)
Sample side column: Direct connection of the following three columns (1) to (3) (all manufactured by Tosoh Corp.)
(1) TSK-GEL GMHXL 7.8 mm×300 mm
(2) TSK-GEL G4000HXL 7.8 mm×300 mm
(3) TSK-GEL G2000HXL 7.8 mm×300 mm
Reference side column: TSK-GEL G1000HXL 7.8 mm×300 mm
Thermostatic chamber temperature: 40° C.
Moving-layer: THF
Sample side moving-layer flow rate: 1.0 mL/min
Reference side moving-layer flow rate: 1.0 mL/min
Sample concentration: 0.1% by mass
Sample injection volume: 100 μL
Data sampling time: 5 to 45 minutes after sample injection
Sampling pitch: 300 msec The support apparatus 12 performs a support for quickly determining a plurality of condition parameters that form a reaction condition in the flow reaction process to be performed by the flow reactor 11. The support apparatus 12 has a learning mode and a calculation mode to be used for determining reaction conditions before a target product is manufactured by the flow reactor 11, and an operation mode to be used while a target product is being manufactured by the flow reactor 11.

Details of the support apparatus 12 will be described later with reference to another drawing, but a prediction function generated in advance using measurement data of the flow reaction performed in the reaction section is recorded in the support apparatus 12. The prediction function is generated in the learning mode and the calculation mode. In the operation mode, the soft sensor 38 applies the detection information from the sensors 35 of the sensor section 36 (see FIG. 3) to the prediction function, and calculates a reaction result in the reaction section 23 as an arithmetic reaction result.

The system controller 15 is a member for generally controlling the flow reactor 11. The system controller 15 is connected to each of the above-described pumps of the first supply section 21 and the second supply section 22, the temperature control section 33, and the above-described switching valve of the collecting section 26. The system controller 15 controls the respective flow rates of the first raw material and the second raw material by respectively controlling the rotating speeds of the pumps of the first supply section 21 and the second supply section 22, to thereby control the respective flow velocities of the first raw material and the second raw material directed toward to the reaction section 23. Note that the flow velocity of the first raw material is calculated by X1/X2 in a case where the flow rate of the first raw material sent from the first supply section 21 to the reaction section 23 is X1 (having a unit of m$^3$/sec) and the cross-sectional area of the tube between the first supply section 21 and the reaction section 23 is X2 (having a unit of m$^2$). Similarly, the flow velocity of the second raw material is calculated by X1/X2 in a case where the flow rate of the second raw material sent from the second supply section 22 to the reaction section 23 is X1 and the cross-sectional area of the pipe between the second supply section 22 and the reaction section 23 is X2 (having a unit of m$^2$). The cross-sectional areas of the pipes (cross-sectional areas of the flow paths) are input in advance to the first flow velocimeter 35a, the second flow velocimeter 35b, and the third flow velocimeter 35c described above. The first flow velocimeter 35a, the second flow velocimeter 35b, and the third flow velocimeter 35c calculate the respective flow velocities from the cross-sectional areas and the respective flow rates of the first raw material, the second raw material, and the mixed raw material passing therethrough for detection. The flow rates of the first raw material and the second raw material are obtained from the rotating speeds on the basis of catalog data of the respective pumps that are commercially available in this example. Further, the system controller 15 controls the temperature of the mixed raw material by controlling the temperature control section 33. The system controller 15 controls the switching valve of the collecting section 26 to control opening and closing of a line toward the precipitating part and a line toward the disposal part. In this way, the system controller 15 controls each section of the flow reactor 11 to generally control the flow reactor 11.

The setting section 16 is a member for setting a processing condition (hereinafter, referred to as a reaction condition) of the flow reaction process in the flow reactor 11. The reaction condition corresponds to a combination of a plurality of condition parameters. The setting section 16 has an operating section (not shown), sets reaction condition by input of an operating signal through the operating section, to thereby control the flow reactor 11 to a predetermined reaction condition through the system controller 15. For example, the reaction condition is set by click or selection using a mouse in the operating section and/or input of characters using a keyboard.

The setting section 16 is connected to the support apparatus 12, and in addition to or instead of the operating signal from the operating section described above, in a case where the support apparatus 12 is in the calculation mode and the operation mode to be described later, the support apparatus 12 controls the flow reactor 11 through the system controller 15 under predetermined reaction conditions based on the input from the support apparatus 12. For example, in a case where the support apparatus 12 is in the calculation mode to be described later, the reaction condition is set to a determined reaction condition CS to be described later read from a third storage section 51c (see FIG. 3) to be described later of the support apparatus 12, and thus, the support apparatus 12 controls the flow reactor 11 to a predetermined reaction condition through the system controller 15. Further, in a case where the support apparatus 12 is in the operation mode to be described later, the reaction conditions to be set are calculated using the above-mentioned arithmetic reaction result that is an output signal from the soft sensor 38, and controls the flow reactor 11 through the system controller 15 on the basis of the calculation result. In this way, the setting section 16 has a computing function. The setting section 16 in this example can also provide an input signal to the support apparatus 12 as described later.

The condition parameters set by the setting section 16 may be determined according to the type of the flow reaction process to be performed, and are not particularly limited. For example, the condition parameters may include the flow rates and/or flow velocities of raw materials such as the first raw material and the second raw material, the temperatures of the raw materials fed into the reaction section 23, the reaction temperature, the reaction time, and the like. In this example, the respective flow velocities of the first and second raw materials, the shape of the merging section, the reaction path diameter D32, the reaction path length L32, and the reaction temperature are included therein.

The condition parameters of the flow reaction process may include condition parameters fixed to predetermined constant value (hereinafter, referred to as fixed parameters). The fixed parameters in this example are the concentration of the reactant in the first raw material and the second raw material, and the reaction path length L32. The concentration of the reactant in the first raw material and the second raw material and the reaction path length L32 are determined in advance in this example, and are not controlled through the system controller 15 (for example, a control for changing the concentration to a higher value or a control for changing the concentration to a lower value is not performed). As described above, in the flow reaction, the control by the system controller 15 is not performed, and condition parameters to be changed in, for example, the raw material preparation process and/or the assembly process of the flow reactor 11 may be included.

Figure 2:
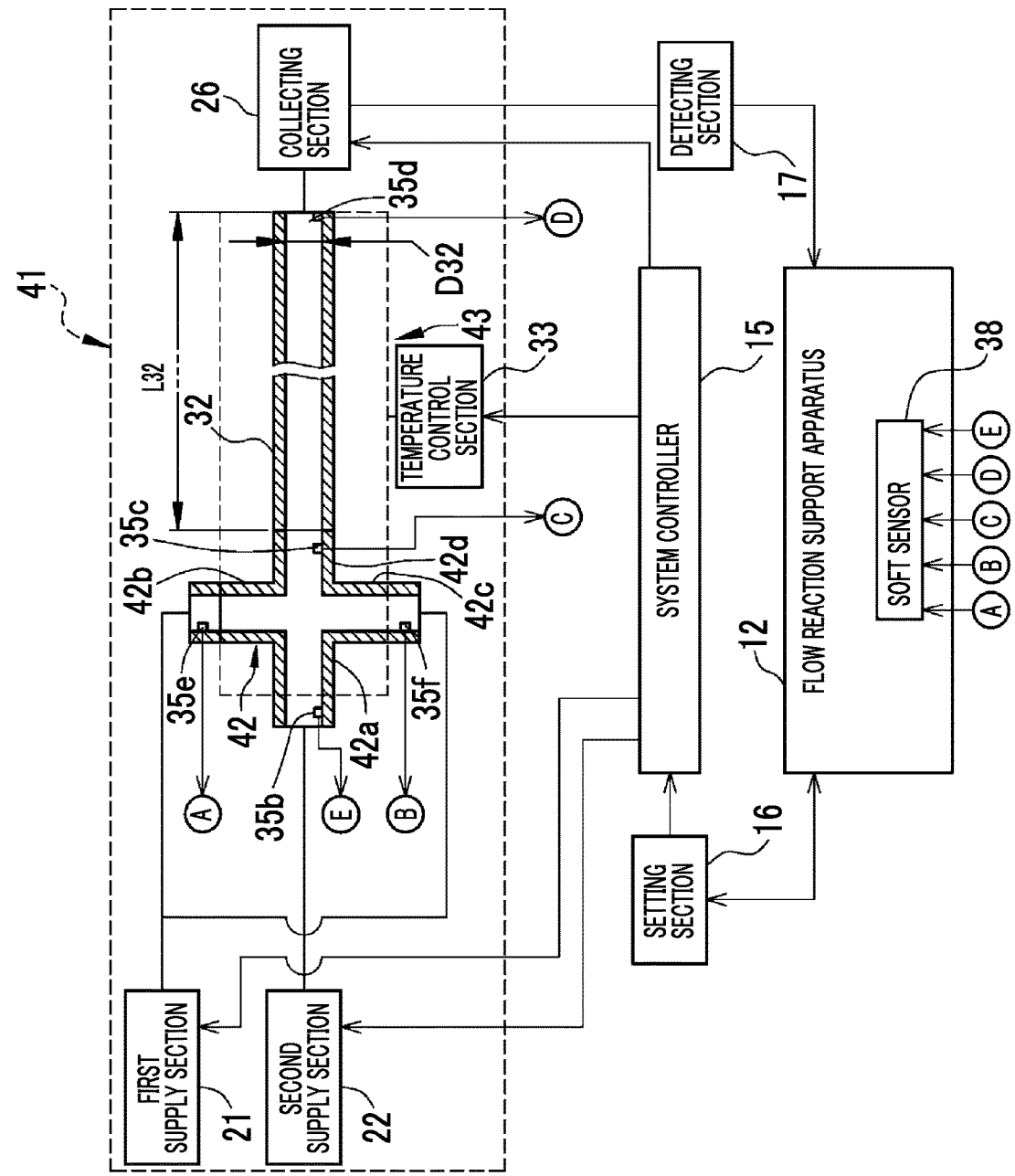
FIG. 2 is a schematic diagram showing another flow reactor.

In the flow reaction facility 10, the flow reactor 11 may be replaced with another flow reactor. For example, in this example, the flow reactor 41 shown in FIG. 2 is also used in the flow reaction facility 10. The flow reactor 41 includes a reaction section 43 in which the merging section 31 is replaced with a merging section 42. Further, in FIG. 2, the same members as those in FIG. 1 are denoted by the same reference numerals as those in FIG. 1, and description thereof will not be repeated.

The merging section 42 is a cross-branched tube, that is, a cross tube. A first tube part 42a of the merging section 42 is connected to the second supply section 22, a second tube part 42b and a third tube part 42c intersecting with the first tube part 42a are connected to the first supply section 21, and the remaining fourth tube part 42d is connected to the reaction section 32. Thus, the guided first raw material and second raw material merge with each other and are sent to the reaction section 32 in a mixed state.

Similar to the flow reactor 11, the flow reactor 41 further comprises one sensor or a plurality of sensors. For example, in this example, five sensors, that is, the above-mentioned second to fourth sensors, fifth and sixth sensors are provided. The fifth sensor is a fourth flow velocimeter 35e, the sixth sensor is a fifth flow velocimeter 35f, and the five sensors form the sensor section 36 (see FIG. 3). In the following description, in a case where the five sensors are not distinguished, they are referred to as sensors 35. Each of the sensors 35 performs the following detection during the flow reaction in the above-mentioned operation mode.

The second flow velocimeter 35b is provided at an inlet of the first tube part 42a in this example. The fourth flow velocimeter 35e is provided at an inlet of the second tube part 42b, detects a flow velocity of one of the first raw materials having divided flows, and outputs the result to the soft sensor 38 of the flow reaction support apparatus 12 as a detection signal. The fifth flow velocimeter 35f is provided at an inlet of the third tube part 42c, detects a flow velocity of the other of the first raw materials having the divided flows, and outputs the result to the soft sensor 38 as a detection signal.

Similar to the first flow velocimeter 35a, the second flow velocimeter 35b, and the third flow velocimeter 35c, the fourth flow velocimeter 35e and the fifth flow velocimeter 35f calculate, in a state where cross-sectional areas of pipes (cross-sectional areas of flow paths) are input in advance, flow velocities from the cross-sectional areas and the flow rates of the first raw materials passing therethrough for detection. Similarly, the fourth flow velocimeter 35e and the fifth flow velocimeter 35f also perform each of the above detections at a regular time interval. The detection time interval is preferably in a range of 1 second or more and 60 seconds or less, and in this example, the detection is performed at an interval of 1 second.

Figure 3A:
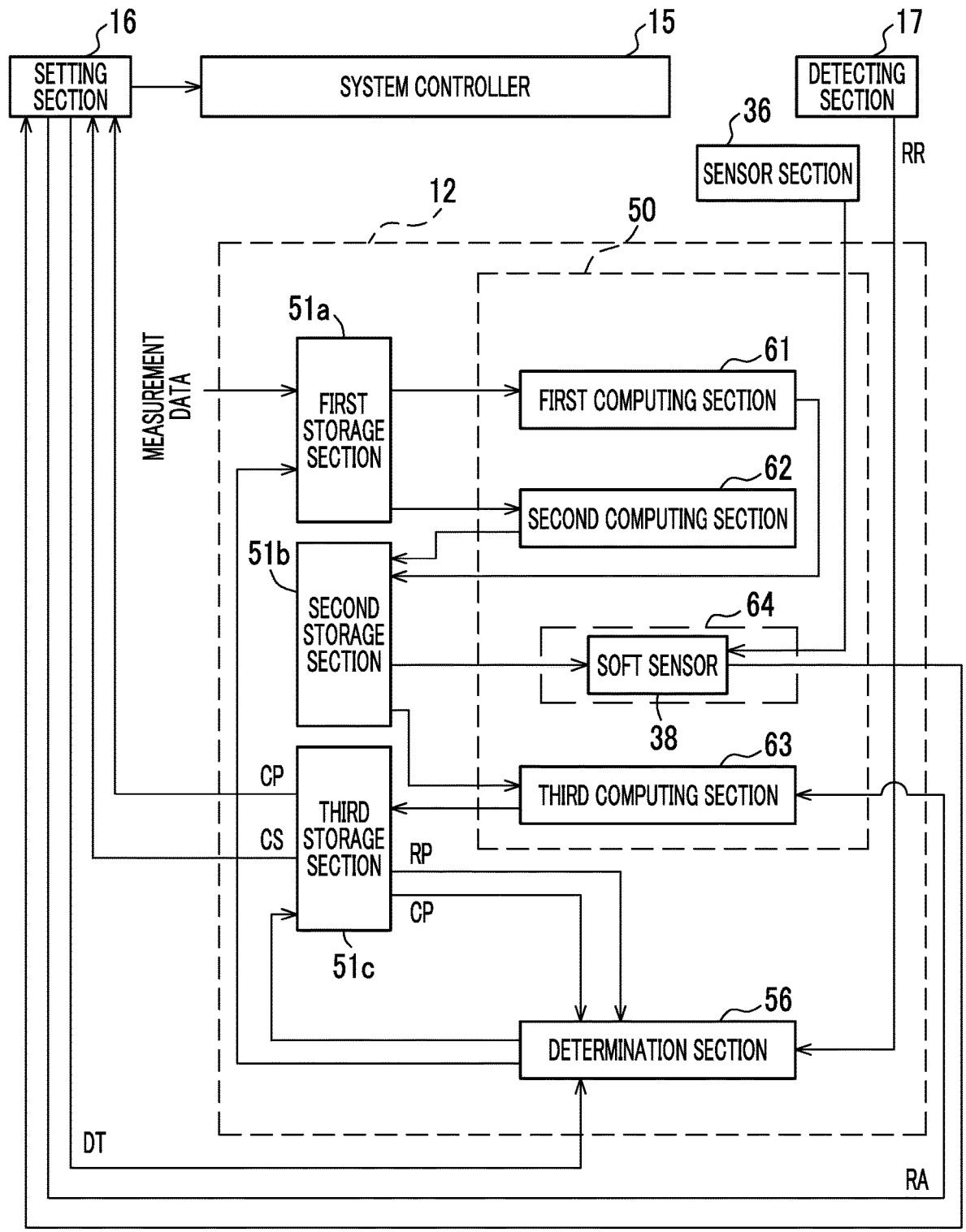
FIG. 3A is a block diagram showing a configuration of a flow reaction support apparatus.

As shown in FIG. 3A, the support apparatus 12 includes a computing section 50, a first storage section 51a to a third storage section 51c, a determination section 56, and the like. In this example, the first storage section 51a to the third storage section 51c are configured separately from the computing section 50, but may be configured as a part of the computing section 50.

The first storage section 51a receives an input of a plurality of pieces of reaction information that have already been carried out in the flow reactor 11, and stores the plurality of pieces of reaction information as measurement data. Each reaction information is a set of reaction data in which a reaction condition and a known reaction result are associated (linked) with each other (see FIG. 4). Accordingly, one reaction condition is associated with one known reaction result. However, the first storage section 51a stores the reaction information in a state of being readable only in the reaction condition. For example, the first storage section 51a stores the reaction condition and the known reaction result in different fields, and also stores association information between the reaction condition and the known reaction result. Alternatively, a field for storing both the reaction condition and the known reaction result and a field for storing only the reaction condition may be provided.

The measurement data configured of the plurality of pieces of reaction information is used as learning data in the computing section 50. The number of the pieces of reaction information forming the measurement data changes according to a determination result of the determination section 56 to be described later. In this example, the first input to the first storage section 51a is 10 pieces of reaction information a to reaction information j, so that the first storage section 51a first stores measurement data configured of 10 pieces of reaction information.

The computing section 50 has a learning mode, a calculation mode, and an operation mode, and performs a target computing process for each mode. The computing section 50 includes a first computing section 61 to a fourth computing section 64, in which the first computing section 61 performs a computing process in the learning mode, and repeats a state in which the computing is paused and a state in which the first storage section 51a is read as described later in the calculation mode. The second computing section 62 and the third computing section 63 are in a pause state in the learning mode, and perform a computing process in the calculation mode. Further, the first computing section 61 to the third computing section 63 are in a pause state in the operation mode. The fourth computing section 64 comprises the above-mentioned soft sensor 38, performs a computing process in the operation mode, and goes into a pause state in the learning mode and the calculation mode.

The first computing section 61 reads out (extracts) the measurement data stored in the first storage section 51a, and uses the read-out measurement data as learning data (training data) to learn a relationship between the reaction condition and the reaction result. Then, the first computing section 61 generates a function in which the reaction condition and the reaction result are associated with each other by learning, and writes the generated function in the second storage section 51b. A plurality of condition parameters forming the reaction condition and result parameters forming the reaction result are respectively variables in the function, and in a case where the condition parameters and the result parameters are already determined, the generation of the function means generation of coefficients in the function.

In this example, the first computing section 61 performs learning using each condition parameter of the reaction condition as an explanatory variable, and the result parameters of the reaction result as objective variables, to thereby form a learned neural network (hereinafter, referred to as an NN) after the first learning is finished. For example, the following functions (1A) and (1B) are generated in the formed NN. The explanatory variables correspond to input variables, and the objective variables correspond to output variables.

$$y1 = w_{u1y1}/[1+\exp\{-(w_{x1u1} \times x_1 + w_{x2u1} \times x_2 + \ldots + w_{x5u1} \times x_5)\}] + w_{u2y1}/[1+\exp\{-(w_{x1u2} \times x_1 + w_{x2u2} \times x_2 + \ldots + w_{x5u2} \times x_5)\}] + \ldots + w_{u20y1}/[1+\exp\{-(w_{x1u20} \times x_1 + w_{x2u20} \times x_2 + \ldots + w_{x5u20} \times x_5)\}] \quad (1A)$$

$$y2 = w_{u1y2}/[1+\exp\{-(w_{x1u1} \times x_1 + w_{x2u1} \times x_2 + \ldots + w_{x5u1} \times x_5)\}] + w_{u2y2}/[1+\exp\{-(w_{x1u2} \times x_1 + w_{x2u2} \times x_2 + \ldots + w_{x5u2} \times x_5)\}] + \ldots + w_{u20y2}/[1+\exp\{-(w_{x1u20} \times x_1 + w_{x2u20} \times x_2 + \ldots + w_{x5u20} \times x_5)\}] \quad (1B)$$

In the above (1A) and (1B), xi (i is a natural number) is a value of a condition parameter, and a maximum value of i is the number of condition parameters. Accordingly, in this example, i is a natural number of 1 or greater and 8 or smaller. ym (m is a natural number) is a value of a result parameter, and a maximum value of m is the number of result parameters. Accordingly, in this example, m is 1 and 2. ul (l is a natural number) is a unit value of an intermediate layer L2 to be described later, and a maximum value of l is the number of units. In this example, l is a natural number of 1 or greater and 20 or smaller. $w_{xiul}$ and $w_{ulym}$ are weighting coefficients. Details are as follows. 1 ml/min may be converted as $1 \times 10^{-6} \times (1/60)$ m/sec, with respect to the flow velocity below.

y1: molecular weight of polystyrene
y2: dispersity of polystyrene
x1 (having a unit of mol/L): concentration of polystyryl-lithium in the first raw material, which is calculated by a calculation formula of A1/B1 in a case where the amount of substance of polystyryllithium (having a unit of mol)) is A1 and the volume of THF (having a unit of L (liter)) is B1
x2 (having a unit of ml/min): flow velocity of the first raw material
x3 (having a unit of mol/L): the concentration of methanol in the second raw material, which is calculated by a calculation formula of A2/B2 in a case where the amount of substance of methanol (having a unit of mol) is A2 and the volume of water (having a unit of L (liter)) is B2
x4 (a dimensionless value): "1" in a case where the merging section is T-shaped, and "2" in a case where the merging section is cross-shape
x5 (having a unit of ml/min): flow velocity of the second raw material
x6 (having a unit of mm): reaction path diameter
x7 (having a unit of m): reaction path length
x8 (having a unit of ° C.): reaction temperature
ul: unit value
$w_{xiul}$: weighting coefficient between xi and ul
ym: value of result parameter
$w_{ulym}$: weighting coefficient between ul and ym The NN may be formed using a commercially available neural network fitting application. For example, in this example, the NN is formed by using MATLAB Neural Fitting tool manufactured by MathWorks. The neural network fitting application is not limited to the above description, and for example, keras package manufactured by RStudio, PBC. which can operate in the R language, or the like, may be used.

Figure 3B:
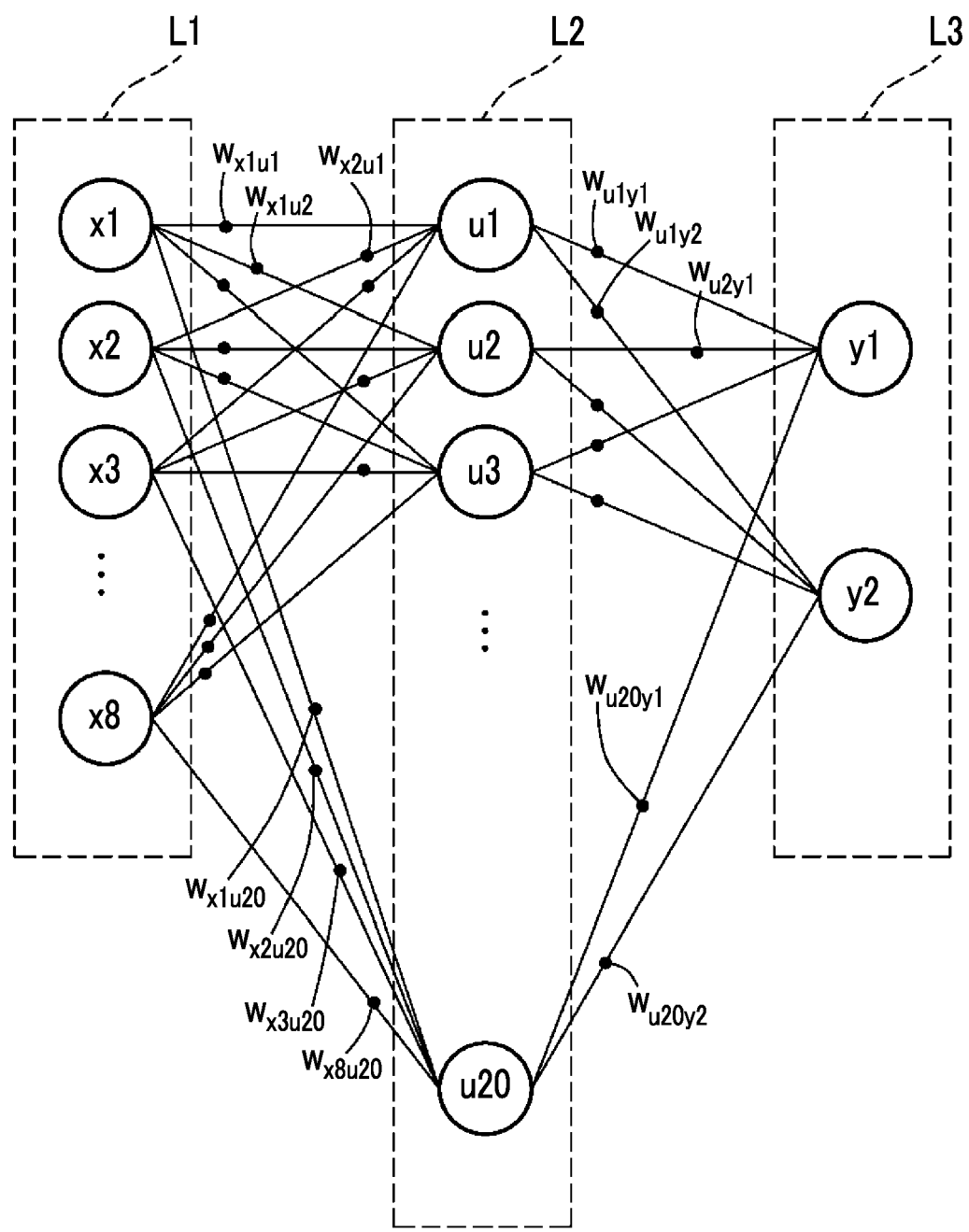
FIG. 3B is a conceptual diagram of a layer structure of a neural network.

The NN has a layer structure of an input layer L1, an intermediate layer (hidden layer) L2, and an output layer L3, and the layer structure realized in this example is shown in FIG. 3B. The input layer L1 includes a value xi of a condition parameter that is an explanatory variable. The intermediate layer L2 includes a unit value ul, which is configured of one layer in this example. Each of the unit values ul is a sum of values obtained by weighting x1 to x8 with a weighting coefficient $w_{xiul}$ corresponding to each of x1 to x8. The output layer L3 includes a value ym of a result parameter that is an objective variable. Each of the values ym of the result parameters is a value obtained by weighting unit values u1 to u20 with a weighting coefficient $w_{ulym}$ corresponding to each of the unit values u1 to u20. In addition, black circles "●" in FIG. 3B indicate the weighting coefficients $w_{xiul}$ and $w_{ulym}$. However, the layer structure of the NN is not limited to this example.

The computing section 50 shown in FIG. 3A switches the learning mode to the calculation mode in a case where a function is written in the second storage section 51b by the first computing section 61. In the calculation mode, the second computing section 62 reads out a reaction condition of measurement data from the first storage section 51a, generates a condition data set including a plurality of reaction conditions whose reaction results are unknown on the basis of the read-out reaction condition, and writes the generated condition data set in the second storage section 51b. The condition data set may include the read-out reaction conditions whose reaction results are known, which is the case in this example.

The second computing section 62 generates the condition data set by taking a value of at least one condition parameter among a plurality of condition parameters that form the reaction condition and generating a reaction condition whose reaction result is unknown. For example, with respect to the flow velocity of the first raw material among the plurality of condition parameters, in a case where the flow velocity of the first raw material within the read-out reaction condition is 1 ml/min, 10 ml/min, 11 ml/min, 20 ml/min, and 100 ml/min, for example, since the reaction result in a case where the flow velocity is 2 ml/min, 5 ml/min, 6 ml/min, or the like is unknown, the reaction condition having these values is generated.

The value of the condition parameter generated in a state of the reaction condition having an unknown reaction result is a value between a minimum value and a maximum value in the condition parameters of the reaction condition read-out from the first storage section 51a, or may include the minimum value and the maximum value in addition thereto. For example, in the above example, since the minimum value of the flow velocity of the first raw material is 1 ml/min and the maximum value thereof is 100 ml/min, a plurality of condition parameter values are generated between these two values, and in this example, the minimum value of 1 ml/min and the maximum value of 100 ml/min are also included in addition thereto. Furthermore, it is preferable that the plurality of values between the maximum value and the minimum value are values obtained by dividing a difference value between the maximum value and the minimum value at an equal interval, and in this example, the flow velocity of the first raw material has values of an interval of 1 ml/min as described later (see FIG. 5).

A condition parameter of which a value is to be taken, among the plurality of condition parameters that form the reaction condition, is set to a condition parameter that can be determined to be changeable in the flow reactor 11. Accordingly, values are not taken with respect to fixed parameters. In this example, a plurality of reaction conditions having values respectively taken with respect to the flow velocities of the first raw material and the second raw material, the type of the merging section (the merging section 31 and the merging section 42), the reaction path diameter D32, and the reaction temperature, are generated (see FIG. 5).

The second storage section 51b stores the function output from the first computing section 61 and the condition data set output from the second computing section 62. In addition, in this example, the second computing section 62 generates the condition data set, but the condition data set may be generated using another computer such as a personal computer.

The third computing section 63 reads out the function and the condition data set from the second storage section 51b, generates a prediction data set, and writes the generated prediction data set in the third storage section 51c. The prediction data set includes a plurality of pieces of prediction information. The prediction information is prediction data in which a prediction result obtained by predicting a reaction result for each reaction condition of the condition data set is associated with the reaction condition. Accordingly, the number of pieces of prediction information is equal to the number of the reaction conditions in the condition data set. The prediction is a computing process performed using the read-out function.

The third computing section 63 specifies and extracts prediction information indicating the best prediction result from the plurality of pieces of prediction information. Then, the third computing section 63 writes the reaction condition of the extracted prediction information as an extracted reaction condition CP in the third storage section 51c, and writes the prediction result RP of the extracted prediction information in association with the extracted reaction condition CP in the third storage section 51c.

A target reaction result (hereinafter, referred to as a target result) RA is input to the third computing section 63 in advance by an operating signal by, for example, an input in the operating section of the setting section 16 in this example. The third computing section 63 compares the target result RA with the prediction result of each piece of prediction information of the prediction data set, and specifies a prediction result that is closest to the target result RA among the plurality of prediction results (having the smallest difference from the target result RA) as the "best prediction result". In a case where there is the same prediction result as the target result RA, the prediction result is specified as the "best prediction result".

Further, in a case where there are a plurality of prediction results that are closest to the target result RA, measurement data is read out from the first storage section 51a, and the "best prediction result" is specified according to the following process with reference to the reaction condition of the measurement data whose reaction result is the closest to the target result RA. First, in a case where the condition parameters of each piece of prediction information of the prediction data set are x1 to x8, the result parameter is y1, and contributions to y1 are a1 to a8, a1 to a8 are defined by the following equations (1C) to (1J).

$$a1 = w_{x1u1} \times w_{u1y1} + w_{x1u2} \times w_{u2y1} + w_{x1u3} \times w_{u3y1} + \ldots + w_{x1ul} \times w_{uly1} \quad (1C)$$

$$a2 = w_{x2u1} \times w_{u1y1} + w_{x2u2} \times w_{u2y1} + w_{x2u3} \times w_{u3y1} + \ldots + w_{x2ul} \times w_{uly1} \quad (1D)$$

$$a3 = w_{x3u1} \times w_{u1y1} + w_{x3u2} \times w_{u2y1} + w_{x3u3} \times w_{u3y1} + \ldots + w_{x3ul} \times w_{uly1} \quad (1E)$$

$$a4 = w_{x4u1} \times w_{u1y1} + w_{x4u2} \times w_{u2y1} + w_{x4u3} \times w_{u3y1} + \ldots + w_{x4ul} \times w_{uly1} \quad (1F)$$

$$a5 = w_{x5u1} \times w_{u1y1} + w_{x5u2} \times w_{u2y1} + w_{x5u3} \times w_{u3y1} + \ldots + w_{x5ul} \times w_{uly1} \quad (1G)$$

$$a6 = w_{x6u1} \times w_{u1y1} + w_{x6u2} \times w_{u2y1} + w_{x6u3} \times w_{u3y1} + \ldots + w_{x6ul} \times w_{uly1} \quad (1H)$$

$$a7 = w_{x7u1} \times w_{u1y1} + w_{x7u2} \times w_{u2y1} + w_{x7u3} \times w_{u3y1} + \ldots + w_{x7ul} \times w_{u1y1} \quad (1I)$$

$$a8 = w_{x8u1} \times w_{u1y1} + w_{x8u2} \times w_{u2y1} + w_{x8u3} \times w_{u3y1} + \ldots + w_{x8ul} \times w_{u1y1} \quad (1J)$$

Here, if a sign in a case where each of a1 to a8 is obtained is positive, a positive contribution is given to the prediction result, and if the sign is negative, a negative contribution is given to the prediction result, in which the larger the absolute value, the higher the contribution to the prediction result.

Subsequently, the reaction result closest to the target result RA and the reaction condition are selected from the measurement data, and when the reaction result is denoted as y1$n$, an absolute value of a difference between y1$n$ and the target result RA is calculated by a calculation formula of |RA−y1$n$|/RA. Then, attention is paid to the magnitudes of absolute values of a1 to a8. For example, in a case where the absolute value of a1 is the largest among the absolute values of a1 to a8, the "best prediction result" is specified by the following four cases of <A> to <D>.

<A> Case where the difference between y1$n$ and RA and y1RA−y1$n$/y1RA are both positive, and a1 is positive In a case where y1$n$ is increased in the positive direction, y1$n$ approaches RA. Accordingly, a prediction result having condition parameters having the largest value in the positive direction compared with the value a1 of the condition parameter of the reaction condition closest to the target result RA in the measurement data is specified as the "best prediction result".

<B> Case where the difference between y1$n$ and RA and y1RA−y1$n$/y1RA are both positive, and a1 is negative In a case where y1$n$ is increased in the positive direction, y1$n$ approaches RA. Accordingly, a prediction result having condition parameters having the largest value in the negative direction compared with the value a1 of the condition parameter of the reaction condition closest to the target result RA in the measurement data is specified as the "best prediction result".

<C> Case where the difference between y1$n$ and RA and y1RA−y1$n$/y1RA are both negative, and a1 is positive In a case where y1$n$ is increased in the negative direction, y1$n$ approaches RA. Accordingly, a prediction result having condition parameters having the largest value in the negative direction compared with the value a1 of the condition parameter of the reaction condition closest to the target result RA in the measurement data is specified as the "best prediction result".

<D> Case where the difference between y1$n$ and RA and y1RA−y1$n$/y1RA are both negative, and a1 is negative In a case where y1$n$ is increased in the negative direction, y1$n$ approaches RA. Accordingly, a prediction result having condition parameters having the largest value in the positive direction compared with the value a1 of the condition parameter of the reaction condition closest to the target result RA in the measurement data is specified as the "best prediction result".

In a case where there are a plurality of result parameters of the reaction result, the target result RA is input in a state where the plurality of result parameters are weighted, and the third computing section 63 specifies the "best prediction result" on the basis of the weights. The specification based on the weights may be, for example, a first method of performing the specification using only the result parameter having the largest weight, or may be a second method of narrowing down, for example, a plurality of candidates from the prediction results closest to the target result RA with the result parameter having the largest weight and specifying the prediction result closest to the target result RA in the result parameters having low weighting ranks among the narrowed-down prediction results as the "best prediction result". In this example, the specification is performed by the second method. The target result RA in this example has a molecular weight of 25,200 and a dispersity of 1.03 or less.

The third storage section 51$c$ stores the prediction data set output from the third computing section 63, the extracted reaction condition CP, and the prediction result RP associated with the extracted reaction condition CP. The prediction data set, the extracted reaction condition CP, and the prediction result RP are stored individually in a readable state.

The setting section 16 reads out the extracted reaction condition CP from the third storage section 51$c$. The extracted reaction condition CP input from the third computing section 63 of the computing section 50 through the third storage section 51$c$ in this way is set as an input signal, and the extracted reaction condition CP is set as a reaction condition in the flow reactor 11. The detecting section 17 outputs a reaction result (hereinafter, referred to as a measurement result) RR of the flow reaction process performed under the extracted reaction condition CP to the determination section 56, as described above.

The determination section 56 reads out the prediction result RP associated with the extracted reaction condition CP from the third storage section 51$c$, compares the prediction result RP with the measurement result RR input from the detecting section 17, and calculates a difference DR between the prediction result RP and the measurement result RR. In this example, the difference DR is calculated by a formula |RP−RR|/RR, but as long as a value that can be used as an index of the certainty of the prediction result RP is calculated, the method of calculating the difference DR is not particularly limited.

An allowable range DT of the difference is input to the determination section 56 in advance as an operating signal by, for example, an input in the operating section of the setting section 16 in this example. The determination section 56 determines whether the difference DR is within the allowable range DT. The allowable range DT is set to 1% in this example, but the allowable range may be appropriately set according to the type of the result parameter. The allowable range DT (having a unit of %) may be calculated by a calculation formula of (|RP−RR|/RR)×100.

In a case where it is determined that the difference DR is within the allowable range DT, the determination section 56 sets the extracted reaction condition CP in the reaction condition group of the prediction data set stored in the third storage section 51$c$ as a reaction condition (hereinafter, referred to as a determined reaction condition) CS of the flow reaction process to be performed by the flow reactor 11, and writes the result in the third storage section 51. The reaction condition group of the prediction data set stored in the third storage section 51$c$, including the setting of the extracted reaction condition CP as the determined reaction condition CS, may be written in the third storage section 51$c$ as a reaction data set to be used in the flow reaction process of the flow reactor 11, which is the case in this example.

In this example, the determination section 56 stores the reaction data set in the third storage section 51$c$ in a readable state for each reaction condition. In this example, the third storage section 51$c$ has an area where the prediction data set is stored and an area where the reaction information data set is stored, but as long as the reaction data set is stored in a readable state for each reaction condition, the determination section 56 may rewrite the reaction condition group of the prediction data set to the reaction data set. In that case, the third computing section 63 causes the third storage section 51c to store the prediction data set in advance in a readable state for each reaction condition. Further, in this example, the reaction condition data set is stored in the third storage section 51c, but a fourth storage section (not shown) may be further provided, and the reaction condition data set may be stored in the fourth storage section.

In a case where it is determined that the difference DR is not within the allowable range DR, the determination section 56 reads out the extracted reaction condition CP from the third storage section 51c, and generates reaction information in which the extracted reaction condition CP and the measurement result RR are associated with each other. Then, the generated reaction information is written in the first storage section 51a as a part of measurement data. By this writing, the measurement data in the first storage section 51a is rewritten, and the number of pieces of reaction information that form the measurement data changes as described above. In this example, as described above, ten pieces of reaction information are stored in the first storage section 51a by the first input, one piece of reaction information is added by one writing of the determination section 56, and new measurement data configured of eleven pieces of reaction information is written in the first storage section 51a.

In this example, the first computing section 61 repeats the pause state and the reading of the first storage section 51a in the calculation mode, as described above. Specifically, the first computing section 61 reads the measurement data of the first storage section 51a at a preset time interval, and determines whether or not the previously read measurement data is rewritten to new measurement data.

In a case where the first computing section 61 determines that the measurement data in the first storage section 51a is not be rewritten, the computing section 50 continues the calculation mode. In a case where it is determined that the data is rewritten, the computing section 50 switches the calculation mode to the learning mode, and the first computing section 61 performs the next learning using new measurement data as learning data, generates a new function, and rewrites a function stored in the second storage section 51b to the new function. The generation of the new function and the rewriting to the new function mean generation of a new coefficient in the function and rewriting of a coefficient in the function. For example, the coefficients of the functions (1A) and (1B) described above are rewritten, and the weighting coefficient $w_{xiul}$ is rewritten to $w2_{xiul}$. In this way, the following functions of (2A) and (2B) are generated.

$$y1 = w2_{u1y1}/[1+\exp\{-(w2_{x1u1} \times x_1 + w2_{x2u1} \times x_2 + \ldots + w2_{x5u1} \times x_5)\}] + w2_{u2y1}/[1+\exp\{-(w2_{x1u2} \times x_1 + w2_{x2u2} \times x_2 + \ldots + w2_{x5u2} \times x_5)\}] + \ldots + w2_{u20y1}/[1+\exp\{-(w2_{x1u20} \times x_1 + w2_{x2u20} \times x_2 + \ldots + w2_{x5u20} \times x_5)\}] \quad (2A)$$

$$y2 = w2_{u1y2}/[1+\exp\{-(w2_{x1u1} \times x_1 + w2_{x2u1} \times x_2 + \ldots + w2_{x5u1} \times x_5)\}] + w2_{u2y2}/[1+\exp\{-(w2_{x1u2} \times x_1 + w2_{x2u2} \times x_2 + \ldots + w2_{x5u2} \times x_5)\}] + \ldots + w2_{u20y2}/[1+\exp\{-(w2_{x1u20} \times x_1 + w2_{x2u20} \times x_2 + \ldots + w2_{x5u20} \times x_5)\}] \quad (2B)$$

Further, in a case where new measurement data is generated, similarly, the second computing section 62 newly generates a condition data set.

The fourth computing section 64 comprises the above-mentioned soft sensor 38. The fourth computing section 64 reads out the prediction function written in the second storage section 51b. The soft sensor 38 applies (fits) the detection information from the sensor 35 in a case where the prediction function is read out, and calculates the reaction result in a case where the flow reaction is performed under these reaction conditions as an arithmetic reaction result. As described above, the fourth computing section 64 is an example of a prediction computing section that calculates a predicted reaction result as an arithmetic reaction result. The target reaction result is input in advance to the fourth computing section 64, and in a case where a difference between the reaction result and the arithmetic reaction result calculated by the soft sensor 38 is within a preset allowable range, the computation enters a pause state. In a case where the difference is not within the allowable range, a reset signal for newly setting the reaction condition is output to the setting section 16.

The setting section 16 is configured that the distance from each of the sensors 35 (in this example, the first flow velocimeter to the fifth flow velocimeter 35a to 35c, 35e, 35f, and the thermometer 35d) that form the sensor section 36 to the above-mentioned switching valve is input in advance thereto. The setting section 16 calculates a switching timing of the switching valve from these distances, the flow velocity of the first raw material, and the flow velocity of the second raw material. On the basis of the calculation result, the setting section 16 switches the switching valve through the system controller 15.

FIG. 4 shows measurement data stored by the first input, and as described above, in this example, the measurement data includes 10 pieces of reaction information a to reaction information j. As shown in FIG. 4, the measurement data stored in the first storage section 51a stores a plurality of pieces of reaction information in a table structure in this example. Specifically, the types of reaction information are arranged in vertical sections, and the types of reaction information, reaction conditions, and reaction results are arranged in horizontal sections. However, the vertical sections and the horizontal sections may be reversed.

A storage form of the measurement data in the first storage section 51a is not limited to the table structure, and any form may be used as long as the reaction condition and the reaction result are associated with each other. Accordingly, for example, any form in which respective fields for the reaction conditions and the reaction results are provided and stored may be used.

As shown in FIG. 5, the condition data set generated by the second computing section 62 also has a table structure in this example, and accordingly, a condition data set having the table structure is stored in the second storage section 51b. Specifically, different reaction conditions are arranged in vertical sections, and condition parameters are arranged in horizontal sections. However, the vertical sections and the horizontal sections may be reversed. Further, the form of the condition data set is not limited to the table structure like the form of the measurement data, and any form in which the condition data set is generated to be individually readable for each reaction condition and stored in the second storage section 51b may be used.

FIG. 5 shows a condition data set generated on the basis of the first measurement data. In the condition data set, condition parameters other than fixed parameters include, in this example, a maximum value, a minimum value, and values obtained by dividing a difference value between the maximum value and the minimum value at an equal interval, as described above. For example, the flow velocity of the first raw material corresponds to values obtained by dividing a difference value between the minimum value of 1 ml/min and the maximum value of 100 ml/min at an interval of 1 ml/min, and the flow velocity of the second raw material corresponds to values obtained by dividing a difference between the minimum value of 0.6 ml/min and the maximum value of 55.0 ml/min at an interval of 0.1 ml/min. The merging section has two shapes, that is, the merging section 31 and the merging section 42. The reaction path diameter D32 corresponds to values obtained by dividing a difference value between the minimum value of 1 mm and the maximum value of 10 mm at an interval of 1 mm, and the reaction temperature corresponds to values obtained by dividing a difference between the minimum value (lowest value) of 1° C. and the maximum value (largest value) of 10° C. at an interval of 1° C. Here, the interval in a case where the values are obtained by the division at an equal interval is not limited to this example.

As shown in FIG. 6, the prediction data set generated by the third computing section 63 also has a table structure in this example, and accordingly, the prediction data set having the table structure is stored in the third storage section 51c. Specifically, the types of prediction information are arranged in vertical sections, and condition parameters of reaction conditions and result parameters that are prediction results are arranged in horizontal sections. However, the vertical sections and the horizontal sections may be reversed. The form of the prediction data set is not limited to the table structure like the form of the measurement data, and any form in which the reaction conditions and the prediction results are associated with each other and at least the extracted reaction condition CP is generated in a readable form and is stored in the third storage section 51c may be used.

FIG. 6 shows a prediction data set generated on the basis of the condition data set of FIG. 5. In this example, two result parameters are weighted as described above, and the weight of the molecular weight is made larger than that of the dispersity. In this example, as shown in FIG. 6, for the molecular weight having the larger weight, the molecular weights of a prediction information number (hereinafter, referred to as prediction information No.) 6050 and prediction information No. 8000 are 24870, and are closest to the target result RA compared with other prediction information Nos., in which their values are the same. Then, among the prediction information No. 6050 and the prediction information No. 8000, the prediction information No. 6050 is closer to the target result RA for a dispersity where the weighting is lower than the molecular weight. Accordingly, the third computing section 63 specifies that the prediction result of the prediction information No. 6050 as the above-mentioned "best prediction result", and specifies the reaction condition of the prediction information No. 6050 as the extracted reaction condition CP. Then, the third computing section 63 causes the third storage section 51c to store the extracted reaction condition CP and the prediction result associated with the extracted reaction condition CP in a state where a record indicating the extracted reaction condition CP is given to the reaction condition of the prediction information No. 6050 (in Table 6, for ease of description, "*" is attached next to the prediction information No.).

The determination section 56 generates comparison data in a case where comparison computing of the prediction result RP and the measurement result RR is performed. Further, the determination section 56 has a comparison data storage section (not shown) that stores the comparison data. FIG. 7 shows comparison data in a case where the first comparison computing is performed. The comparison data is generated in a table structure in which the result parameters of the prediction result RP and the result parameters of the measurement result RR are arranged. In this example, the prediction result RP and the measurement result RR are disposed in vertical sections and the two result parameters of the dispersity and the molecular weight are disposed in horizontal sections, but the vertical sections and the horizontal sections may be reversed. Further, as long as the same result parameters of the measurement result RP and the measurement result RR are stored in the comparison data storage section in a readable state, the storage form is not limited to the table structure.

The determination section 56 calculates a molecular weight difference DR and a dispersity difference DR, respectively, using the comparison data, by the above-described calculation formulas. For example, in a case where the comparison data shown in FIG. 7 is used, the molecular weight difference DR is calculated as 9.9891 and the dispersity difference DR is calculated as 3.5107.

Figure 8:
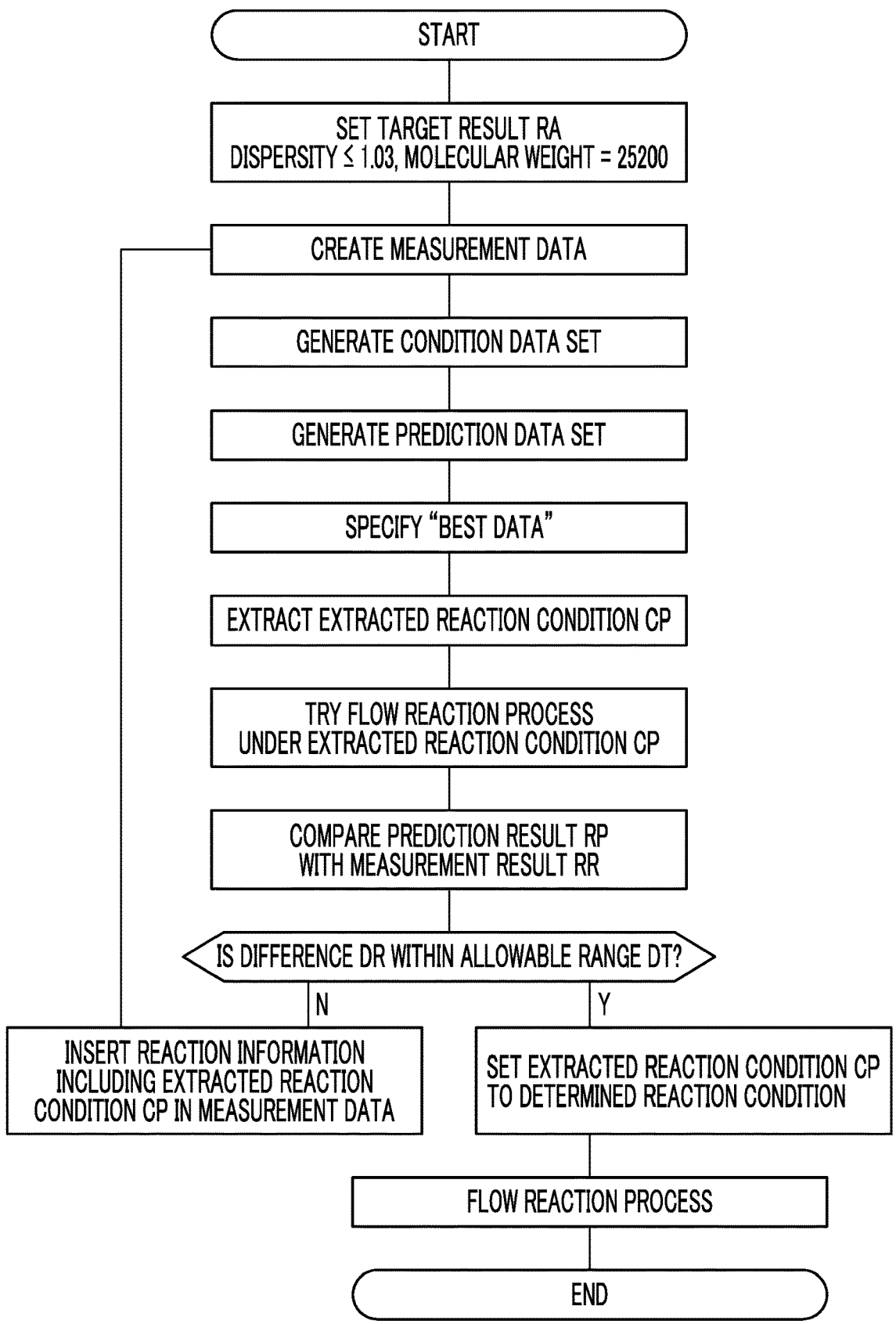
FIG. 8 is a flowchart showing a procedure of performing a flow reaction process.

An operation of the above configuration will be described. As shown in FIG. 8, first, the target result RA is set. As described above, the target result RA of this example is set so that dispersity≤1.03 and molecular weight=25,200. Then, measurement data is created. Note that the order of the setting of the target result RA and the creation of the measurement data may be reversed.

The measurement data is created by performing the flow reaction process a plurality of times using the flow reactor 11 and the flow reactor 41, and by associating the respective reaction results with the reaction conditions. The flow reaction process for creating the measurement data is performed by inputting condition parameters through the operating section of the setting section 16 and causing the system controller 15 to perform a control on the basis of the input signal. In this example, the created measurement data is input through the operating section of the setting section 16 (see FIGS. 1 to 3), and the input signal is written in the first storage section 51a. In this example, as described above, 10 pieces of reaction information a to j in the first input are used as the measurement data (the first measurement data) (see FIG. 4).

The support apparatus 12 sets the learning mode, and thus, the first computing section 61 reads out the first measurement data from the first storage section 51a. The measurement data may be output from the setting section 16 to the first computing section 61 without provision (without interposition) of the first storage section 51a. In this way, the first computing section 61 to which the first measurement data is input performs, using the first measurement data as learning data, a computing of learning a relationship between the reaction condition and the reaction result on the basis of the learning data. Then, the first computing section 61 generates a function of the condition parameter and the result parameter, and writes the generated function in the second storage section 51b.

After the function is written in the second storage section 51b, the support apparatus 12 switches the learning mode to the calculation mode, and thus, the second computing section 62 reads out the measurement data from the first storage section 51a. The second computing section 62 takes a value of a condition parameter other than fixed parameters on the basis of the reaction condition of the measurement data, specifically, on the basis of the value of each condition parameter, and generates a condition data set including a plurality of different reaction conditions (see FIG. 5). The second computing section 62 regards the condition parameters having the same content in all the reaction information in the measurement data as the fixed parameters. The generated condition data set is written in the second storage section 51b in a readable state for each reaction condition.

In this example, as described above, the condition data set is generated with the condition parameters dividedly including the maximum value, the minimum value, and the values obtained by dividing the difference value between the maximum value and the minimum value at an equal interval. Since the flow velocity of the first raw material has 100 types, the flow velocity of the second raw material has 545 types, the shape of the merging section has 2 types, the reaction path diameter D32 has 10 types, and the reaction temperature has 11 types, the number of reaction conditions of the condition data set is 100×545×2×10×11, which is 11990000 in total.

In a case where the support apparatus 12 can perform learning and calculation in parallel, both computations of the learning in the first computing section 61 and the creation of the condition data set in the second computing section 62 may be performed at the same time.

After the function and the condition data set are written in the second storage section 51*b*, the third computing section 63 reads out the function and the condition data set from the second storage section 51*b*. In addition, without provision (without interposition) of the second storage section 51*b*, the function may be output from the first computing section 61 to the third computing section 63, and the condition data set may be output from the second computing section 62 to the third computing section 63. The third computing section 63 to which the function and the condition data set are input in this way calculates a prediction result using the function for each reaction condition of the read-out condition data set. Then, the prediction data set including a plurality of pieces of prediction information in which the reaction conditions and the prediction results are associated with each other is generated and is written in the third storage section 51*c* (see FIG. 6).

Since the prediction result is calculated for each reaction condition of the condition data set, the number of pieces of prediction information of the generated prediction data set is 11,990,000 in this example, like the number of reaction conditions of the condition data set.

The third computing section 63 specifies the prediction information indicating the "best prediction result" by comparing the target result RA that is input in advance and the prediction result of each piece of prediction information of the prediction data set. The reaction condition of the specified prediction information is extracted as the extracted reaction condition CP (learning and computing step), and the prediction information including the extracted reaction condition CP and the prediction result RP corresponding to the extracted reaction condition is written in the third storage section 51*c* as the extracted reaction condition CP and the prediction result RP associated with the extracted reaction condition CP in the prediction data set.

After the extracted reaction condition CP is written in the third storage section 51*c*, the setting section 16 reads out the extracted reaction condition CP from the third storage section 51*c*. The extracted reaction condition CP may be output from the third computing section 63 to the setting section 16 without provision (without interposition) of the third storage section 51*c*. The setting section 16 to which the extracted reaction condition CP is input in this way causes the flow reactors 11 and 41 to try the flow reaction process under the extracted reaction condition CP. Then, the measurement result RR that is the reaction result of the trial is output to the determination section 56 by the detecting section 17.

The prediction result RP associated with the extracted reaction condition CP written in the third storage section 51*c* is read out by the determination section 56. The prediction result RP may be output from the third computing section 63 to the determination section 56 without interposition of the third storage section 51*c*. The determination section 56 to which the prediction result RP is input in this way compares the prediction result RP with the measurement result RR (the first comparison) to obtain the difference DR (see FIG. 7).

The determination section 56 determines, on the basis of an allowable range DT of the difference (1% in this example) that is input in advance from the setting section 16, whether or not the difference DR is within the allowable range DT. In a case where it is determined that the difference DR is within the allowable range DT, the determination section 56 writes the extracted reaction condition CP in the third storage section 51 as the determined reaction condition CS, and the determination section 56 of the present example further writes the reaction condition group of the prediction data set stored in the third storage section 51*c* in the third storage section 51*c* as a reaction data set to be used in the flow reaction process of the flow reactor 11.

After the extracted reaction condition CP is written as the determined reaction condition CS, the setting section 16 sets the reaction condition in the flow reactor 11 to the determined reaction condition CS, and then, the flow reactor 11 performs a flow reaction for manufacturing a target product. Since the determined reaction condition CS is a reaction condition that is determined to obtain a reaction result that is extremely close to the measurement result RR, the product can be obtained with a target molecular weight and a target dispersity. Further, the determined reaction condition CS is obtained using a computing from a huge number of reaction conditions of, for example, 11,990,000 in this example, and the trial and time of the flow reaction process are greatly shortened as compared with the related art.

In this example, the difference DR obtained from the first comparison data is, as shown in FIG. 7, is 9.989142 in the molecular weight and 2.906355 in the dispersity, which is determined to be outside the allowable range DR. In such a case, the determination section 56 reads out the extracted reaction condition CP from the third storage section 51*c*, and generates reaction information in which the extracted reaction condition CP and the measurement result RR are associated with each other. Then, the generated reaction information is added to the measurement data of the first storage section 51*a* (determination step), and the measurement data of the first storage section 51*a* is rewritten to new measurement data as the second measurement data. By this rewriting, the newly generated second measurement data is stored in the first storage section 51*a* in a state of being configured of all 11 pieces of reaction information a to k (see FIG. 9).

In a case where the second measurement data is stored in the first storage section 51*a*, the computing section 50 switches the calculation mode to the learning mode, and the first computing section 61 performs the second learning. By this learning, the coefficients of the function stored in the second storage section 51*b* are rewritten to new coefficients, and the new function is written in the first storage section 51*a* as the second function.

Further, in a case where the second measurement data is generated, similarly, the second computing section 62 newly generates a condition data set and writes the result in the second storage section 51*b*. Then, the third computing section 63 newly generates a prediction data set on the basis of the second function and the second condition data set stored in the second storage section 51*b*, similar to the previous time, and newly extracts the extracted reaction condition CP and its prediction result RP. Then, the flow reaction process based on the extracted reaction condition CP is tried by the flow reactors 11 and 41, and the determination section 56 compares the new prediction result RP with the new measurement result RR (second comparison), similar to the first time, to newly obtain the difference DR (see FIG. 10).

In a case where it is determined that the current difference DR is within the allowable range DT, the extracted reaction condition CP is set as the determined reaction condition CS, similar to the first time, and then, the flow reaction process under the determined reaction condition is performed in the operation mode as a reaction process for manufacturing a target product. Since the determined reaction condition CS is a reaction condition that is determined to obtain a reaction result that is extremely close to the measurement result RR, the product is obtained with a target molecular weight and a target dispersity. Further, the determined reaction condition CS is obtained from a huge number of reaction condition candidates in the learning and computing step and the determination step that are repeated twice, and the trial and time of the flow reaction process are greatly shortened as compared with the related art.

In a case where it is determined that the difference DR is not within the allowable range DR, the reaction information that is newly generated through the same computing process as in the first time is added to the measurement data of the first storage section 51$a$, and the third measurement data is generated in the first storage section 51$a$. In this way, the learning and computing step and the determination step are repeated until it is determined in the determination step that the difference DR falls within the allowable range DT, and after the difference DR is within the allowable range DT, the flow reaction process is performed under the obtained determined reaction condition CS.

In this example, in the seventh determination step, the difference DR falls within the allowable range DT (see FIG. 11), and the flow reaction process is performed under the seventh extracted reaction condition. In this example, the number of trials including the flow reaction process for creating the first measurement data is only 17 times. Further, the time necessary for each learning and computing step and each determination step is about one hour in this example. In this way, the reaction condition of the flow reaction process, which has many condition parameters and a huge number of combinations thereof, is obtained extremely quickly.

In addition, in the above example, the reaction data set is stored in the third storage section 51$c$. Since the reaction data set is configured of the reaction conditions that are already obtained by going through the learning and computing step and the determination step, even in a case where fixed parameters among the condition parameters are changed or added, or even in a case where the target result RA is changed, the determined reaction condition CS may be quickly found. For example, in a case where the target result RA of the molecular weight is changed from the value in the above example to another value, the determined reaction condition CS can be found by the following method.

First, the target result RA of the molecular weight is input from the setting section 16 to the determination section 56. Further, for example, by a command signal from the setting section 16, the reaction data set of the third storage section 51$c$ is read into the determination section 56, and a prediction result that is closest to the target result RA is specified from the read reaction data set.

In many cases, the reaction condition associated with the prediction result specified in this way may be used as the determined reaction condition CS in a case where the current target result RA is very close to the above example, that is, the previous target result RA. In a case where the current target result RA is distant from the previous target result RA, the reaction condition associated with the specified prediction result is regarded as the previous extracted reaction condition CP, and the determination step is performed in the same manner as in the above example. In a case where it is determined in the determination step that the difference DR is not within the allowable range DT, the learning step and the determination step are repeated, but the trial and time of the flow reaction process until the determined reaction condition CS is found are shortened as compared with the previous time. In this way, for example, even in a case where the target result RA is changed, the determined reaction condition CS can be quickly found, and the flow reaction process can be performed earlier.

In this way, since the condition setting can be performed easily in a flow reaction with many condition parameters, the reaction process can be started quickly, and even in a case where one of a plurality of condition parameters has to be changed for any reason, it is possible to perform a new reaction process quickly.

After the reaction data set including the determined reaction condition CS is obtained by the above method, the setting section 16 controls the flow reactors 11 and 41 through the system controller 15 under the reaction conditions selected from these reaction data sets, starts manufacturing of a target product, and rewrites the function written in the second storage section 51$b$ as the prediction function.

The distance from each of the sensors 35 to the above-mentioned switching valve is input to the setting section 16 in advance, and the setting section 16 calculates a transit time of the mixed raw material from each of the sensors 35 to the switching valve from the distance and the flow velocity of the first raw material and the flow velocity of the second raw material, which are condition parameters of the reaction condition, thereby calculating the next switching timing of the switching valve.

In a case where the function of the second storage section 51$b$ is rewritten as the prediction function, the support apparatus 12 sets the computing section 50 to the operation mode. While the target product is being manufactured in the flow reaction process, the system controller 15 causes the line toward the precipitating part to be opened and the line toward the disposal part to be closed using the above-mentioned switching valve of the collecting section 26.

During the flow reaction process for manufacturing the target product (flow reaction step), the sensor 35 of the sensor section 36 detects the respective flow velocities of the first raw material, the second raw material, and the mixed raw material at a regular time interval (sensing step), and outputs the detection information to the soft sensor 38. The fourth computing section 64 reads out the prediction function written in the second storage section, and the soft sensor 38 applies (fits) the detection information from the sensor 35 to the prediction function, and calculates a reaction result in a case where the flow reaction is performed under this reaction condition as an arithmetic reaction result. In this way, the fourth computing section 64 having the soft sensor 38 monitors the flow reaction state in the reaction section 23, and calculates the arithmetic reaction result using the function used by the third computing section 63 of the computing section 50 in a case where the determination unit 56 determines that the difference degree DR is within the allowable range DT. The fourth computing section 64 compares the target reaction result that is input in advance with the arithmetic reaction result calculated by the soft sensor 38, and in a case where a difference therebetween is within the preset allowable range, the fourth computing section 64 causes the computation to enter a pause state, and awaits an input of the next detection information from the sensor 35. Further, in a case where the difference is not within the allowable range, a reset signal for newly setting the reaction condition is output to the setting section 16, or a reaction condition to be newly set is output thereto as a reset signal. As the signal for newly setting the reaction condition, for example, there is a signal for resetting to a reaction condition set in the setting section 16 at the start of the flow reaction for manufacturing a target product.

For example, while the flow reaction process is being performed under the determined reaction condition CS using the flow reactor 11 shown in FIG. 1, a flow velocity Va of the first raw material that forms the determined reaction condition CS is changed to Vb that is different from Va. In this case, the flow velocity Vb is output as detection information from the first flow velocimeter 35a to the soft sensor 38. The soft sensor 38 applies the flow velocity Vb to the prediction function, and calculates a molecular weight and a dispersity in a case where the flow reaction process is performed at the flow velocity Vb as an arithmetic reaction result. It is determined whether or not the arithmetic reaction result satisfies the above allowable range, and in a case where the arithmetic reaction result satisfies the allowable range, the computation enters the pause state, and the input of the next detection information from the sensor 35 is awaited. In a case where the arithmetic reaction result does not satisfy the allowable range, the fourth computing section 64 outputs a reset signal for resetting the reaction condition (in this example, the reaction conditions of the flow velocity Va) set at the start of the flow reaction for manufacturing the target product, for example, to the setting section 16. The reset signal input to the setting section 16 means that the flow velocity Vb is returned to Va, and the setting section 16 controls the pump of the first supply section 21 through the system controller 15 to enter a state where the flow velocity of the first raw material is Va, on the basis of the input of the reset signal obtained using the arithmetic reaction result.

In the above example, the reset signal for setting the flow velocity Vb of the first raw material to Va is output, but the present disclosure is not limited thereto. For example, a reaction condition configured of other condition parameters in which the target product is obtained, among reaction conditions having the flow velocity Vb, may be output as a reset signal.

In performing a control based on the arithmetic reaction result, the system controller 15 switches the above-mentioned switching valve of the collecting section 26 to close the line toward the precipitating part and open the line toward the disposal part. In the example in which the flow velocity of the first raw material changes using the flow reactor 11 shown in FIG. 1, the switching timing is, for example, calculated by the setting section 16 on the basis of the distance from an upstream end of the reaction section 23 provided with the first flow velocimeter 35a and the second flow velocimeter 35b to the switching valve, and the detection information of the first flow velocimeter 35a and the second flow velocimeter 35b, and the switching is performed on the basis of the calculated signal from the setting section 16. However, the detection information from the third flow velocimeter 35c may be used instead of the detection information of the first flow velocimeter 35a and the second flow velocimeter 35b. Further, in the above example, the flow velocity of the first raw material changes, but in a case where the reaction temperature changes, the reaction temperature detected by the thermometer 35d is used as the detection information, and the switching timing of the switching valve is calculated on the basis of the distance from the thermometer 35d to the switching valve instead of the distance from the upstream end of the reaction section 23 to the switching valve.

In a case where the flow velocity of the first raw material is reset to Va on the basis of the reset signal, the switching timing of the switching valve is calculated by the setting section 16 on the basis of a timing when the detection information in the first flow velocimeter 35a becomes the flow velocity Va, and the switching of the switching valve is performed so that the line toward the precipitating part enters the opened state and the line toward the disposal part enters the closed state through the system controller 15. As described above, even in a case where the reaction conditions change during the flow reaction process, the reaction result that follows the change in the reaction conditions is obtained as an arithmetic reaction result, and thus, it is possible to reliably obtain a target product while rapidly changing the reaction conditions on the basis of the arithmetic reaction result. In addition, even in a case where waste is generated due to the change in the reaction conditions, it is possible to reduce the amount thereof.

The above description is an example in which the first raw material and the second raw material are used as the raw materials. However, the number of raw materials is not limited thereto, and may be three or more. Further, in the above example, one flow reaction is performed, but a multi-step reaction in which a plurality of flow reaction processes are combined may be performed. In addition, in the above example, the fourth computing section 64 is provided in the computing section 50, but the fourth computing section 64 may be provided separately from the computing section 50, or only the soft sensor 38 of the fourth computing section 64 may be provided separately from the computing section 50.

Each processing section such as the system controller, the prediction computing section, the computing section, the determination section described above is configured of a memory for storing commands corresponding to respective processes and a processor configured to execute the stored commands. The processor includes a so-called central processing unit (CPU), a programmable logic device of which a circuit configuration is changeable after manufacturing, such as a field-programmable gate array (FPGA), a dedicated electric circuit, which is a processor having a circuit configuration specially designed for executing a specific process, such as an application specific integrated circuit (ASIC), or the like. One processing section may be configured by one type of processor, or may be configured of a combination of two or more processors of the same type or different types (for example, a plurality of FPGAs, a combination of a CPU and an FPGA). As an example in which a plurality of processing sections is configured by one processor, first, as represented by a computer such as a client computer, a server, or the like, there is a form in which one processor is configured by a combination of one or more CPUs and software and the one processor functions as a plurality of processing sections. Second, as represented by a system on chip, or the like, there is a form in which a processor that realizes entire functions of a system including a plurality of processing sections by one integrated circuit (IC) chip is used. As described above, the various processing sections are configured using one or more of the various processors as a hardware structure. Further, as the hardware structure of these various processors, more specifically, an electric circuitry in which circuit elements such as semiconductor elements are combined may be used.

EXPLANATION OF REFERENCES

10: Flow reaction facility
11, 41: Flow reactor
12: Support apparatus
15: System controller
16: Setting section
17: Detecting section
21: First supply section
22: Second supply section
23, 43: Reaction section
26: Collecting section
31, 42: Merging section
31A, 31B: First merging part, second merging part
31$a$ to 31$c$: First tube part to third tube part
32: Reaction section
33: Temperature control section
35: Sensor
35$a$: First flow velocimeter
35$b$: Second flow velocimeter
35$c$: Third flow velocimeter
35$d$: Thermometer
35$e$: Fourth flow velocimeter
35$f$: Fifth flow velocimeter
36: Sensor section
38: Soft sensor
50: Computing section
51$a$ to 51$c$: First storage section to third storage section
56: Determination section
61 to 64: First computing section to fourth computing section
CP: Extracted reaction condition
CS: Determined reaction condition
DT: Allowable range
DR: Difference
L1: Input layer
L2: Intermediate layer
L3: Output layer
xi, x1 to x8: Condition parameter values
ul, u1 to u20: Unit values
ym, y1 to y2: Result parameter values
$w_{xiul}$, $w_{x1u1}$ to $w_{x8u20}$, $w_{ulym}$, $w_{u1y1}$ to $w_{u20y2}$: Weighting coefficients
RA: Target result
RP: Prediction result
RR: Measurement result

What is claimed is:

1. A flow reaction facility comprising:
a reaction section that causes a reaction of a raw material during flow;
a collecting section that collects a product generated by the reaction;
a sensor that detects the reaction condition in the reaction section and outputs the detected reaction condition as detection information; and
at least one memory and at least one processor which function as:
a system controller that control the reaction section under a set reaction condition; and
a prediction computing section configured to apply the detection information from the sensor to a prediction function that is generated in advance using measurement data including a plurality of pieces of reaction information in which a reaction condition whose reaction result is known and the reaction result are associated with each other and calculates a reaction result in the reaction section as an arithmetic reaction result,
wherein the system controller controls the reaction section on the basis of the arithmetic reaction result.

2. The flow reaction facility according to claim 1,
wherein the sensor detects the reaction condition at a regular time interval.

3. The flow reaction facility according to claim 1, wherein the at least one memory and the at least one processor further function as:
a computing section that calculates a prediction result for each reaction condition of a condition data set having a plurality of reaction conditions whose reaction results are unknown using a function generated from the measurement data to generate a prediction data set in which the reaction condition and the prediction result are associated with each other, specifies the prediction result closest to a preset target result among a plurality of the obtained prediction results, and extracts a reaction condition associated with the specified prediction result as an extracted reaction condition; and
a determination section that determines whether or not a difference between the reaction result in a case where the reaction is performed under the extracted reaction condition and the prediction result associated with the extracted reaction condition is within a preset allowable range, adds reaction information in which the extracted reaction condition and the reaction result in a case where the reaction is performed under the extracted reaction condition are associated with each other to the measurement data in a case where the difference is not within the allowable range, and sets the extracted reaction condition as a reaction condition to be used in a flow reaction process in a case where the difference is within the allowable range,
wherein the prediction computing section uses the function used by the computing section as the prediction function in a case where the determination section determines that the difference is within the allowable range.

4. The flow reaction facility according to claim 2, wherein the at least one memory and the at least one processor further function as:
a computing section that calculates a prediction result for each reaction condition of a condition data set having a plurality of reaction conditions whose reaction results are unknown using a function generated from the measurement data to generate a prediction data set in which the reaction condition and the prediction result are associated with each other, specifies the prediction result closest to a preset target result among a plurality of the obtained prediction results, and extracts a reaction condition associated with the specified prediction result as an extracted reaction condition; and
a determination section that determines whether or not a difference between the reaction result in a case where the reaction is performed under the extracted reaction condition and the prediction result associated with the extracted reaction condition is within a preset allowable range, adds reaction information in which the extracted reaction condition and the reaction result in a case where the reaction is performed under the extracted reaction condition are associated with each other to the measurement data in a case where the difference is not within the allowable range, and sets the extracted reaction condition as a reaction condition to be used in a flow reaction process in a case where the difference is within the allowable range,
wherein the prediction computing section uses the function used by the computing section as the prediction function in a case where the determination section determines that the difference is within the allowable range.

5. The flow reaction facility according to claim 1, wherein the reaction condition is any one of a flow rate of the raw material, a flow velocity of the raw material, a concentration of a reactant in the raw material, a temperature of the raw material, a set temperature of the reaction, or a reaction time.

6. The flow reaction facility according to claim 2, wherein the reaction condition is any one of a flow rate of the raw material, a flow velocity of the raw material, a concentration of a reactant in the raw material, a temperature of the raw material, a set temperature of the reaction, or a reaction time.

7. The flow reaction facility according to claim 3, wherein the reaction condition is any one of a flow rate of the raw material, a flow velocity of the raw material, a concentration of a reactant in the raw material, a temperature of the raw material, a set temperature of the reaction, or a reaction time.

8. The flow reaction facility according to claim 1, wherein the reaction result is any one of a yield of a product, a yield of a by-product, a molecular weight of the product, a molecular weight dispersity of the product, or a molar concentration of the product.

9. The flow reaction facility according to claim 2, wherein the reaction result is any one of a yield of a product, a yield of a by-product, a molecular weight of the product, a molecular weight dispersity of the product, or a molar concentration of the product.

10. The flow reaction facility according to claim 3, wherein the reaction result is any one of a yield of a product, a yield of a by-product, a molecular weight of the product, a molecular weight dispersity of the product, or a molar concentration of the product.

11. The flow reaction facility according to claim 4, wherein the reaction result is any one of a yield of a product, a yield of a by-product, a molecular weight of the product, a molecular weight dispersity of the product, or a molar concentration of the product.

12. A flow reaction method comprising:
a flow reaction step of controlling, using at least one memory and at least one processor which function as a system controller that controls a reaction section that causes a reaction of a raw material during flow, the reaction section under a set reaction condition to cause the reaction of the raw material;
a collecting step of collecting a product generated by the reaction;
a sensing step of detecting a reaction condition during the flow reaction step; and
a prediction computing step of applying detection information obtained in the sensing step to a prediction function that is generated in advance using measurement data including a plurality of pieces of reaction information in which a reaction condition whose reaction result is known and the reaction result are associated with each other and calculates a reaction result in the reaction section as an arithmetic reaction result,
wherein the system controller controls the reaction section on the basis of the arithmetic reaction result.

13. The flow reaction method according to claim 12, wherein the sensing step includes detecting the reaction condition at a regular time interval.

14. The flow reaction method according to claim 12, further comprising:
a learning and computing step of calculating a prediction result for each reaction condition of a condition data set having a plurality of reaction conditions whose reaction results are unknown using a function generated from the measurement data to generate a prediction data set in which the reaction condition and the prediction result are associated with each other, specifying the prediction result closest to a preset target result among a plurality of the obtained prediction results, and extracting a reaction condition associated with the specified prediction result as an extracted reaction condition; and
a determination step of determining whether or not a difference between the reaction result in a case where the reaction is performed under the extracted reaction condition and the prediction result associated with the extracted reaction condition is within a preset allowable range, adding reaction information in which the extracted reaction condition and the reaction result in a case where the reaction is performed under the extracted reaction condition are associated with each other to the measurement data in a case where the difference is not within the allowable range, and adding the extracted reaction condition to a reaction condition to be used in a flow reaction process in a case where the difference is within the allowable range,
wherein the learning and computing step and the determination step are newly repeated in a case where the reaction information is added to the measurement data in the determination step, and
in the prediction computing step, the function used by the computing section is used as the prediction function in a case where the determination section determines that the difference is within the allowable range.

15. The flow reaction method according to claim 13, further comprising:
a learning and computing step of calculating a prediction result for each reaction condition of a condition data set having a plurality of reaction conditions whose reaction results are unknown using a function generated from the measurement data to generate a prediction data set in which the reaction condition and the prediction result are associated with each other, specifying the prediction result closest to a preset target result among a plurality of the obtained prediction results, and extracting a reaction condition associated with the specified prediction result as an extracted reaction condition; and
a determination step of determining whether or not a difference between the reaction result in a case where the reaction is performed under the extracted reaction condition and the prediction result associated with the extracted reaction condition is within a preset allowable range, adding reaction information in which the extracted reaction condition and the reaction result in a case where the reaction is performed under the extracted reaction condition are associated with each other to the measurement data in a case where the difference is not within the allowable range, and adding the extracted reaction condition to a reaction condition to be used in a flow reaction process in a case where the difference is within the allowable range,
wherein the learning and computing step and the determination step are newly repeated in a case where the reaction information is added to the measurement data in the determination step, and in the prediction computing step, the function used by the computing section is used as the prediction function in a case where the determination section determines that the difference is within the allowable range.

16. The flow reaction method according to claim 12, wherein the reaction condition is any one of a flow rate of the raw material, a flow velocity of the raw material, a concentration of a reactant in the raw material, a temperature of the raw material, a set temperature of the reaction, or a reaction time.

17. The flow reaction method according to claim 13, wherein the reaction condition is any one of a flow rate of the raw material, a flow velocity of the raw material, a concentration of a reactant in the raw material, a temperature of the raw material, a set temperature of the reaction, or a reaction time.

18. The flow reaction method according to claim 14, wherein the reaction condition is any one of a flow rate of the raw material, a flow velocity of the raw material, a concentration of a reactant in the raw material, a temperature of the raw material, a set temperature of the reaction, or a reaction time.

19. The flow reaction method according to claim 15, wherein the reaction condition is any one of a flow rate of the raw material, a flow velocity of the raw material, a concentration of a reactant in the raw material, a temperature of the raw material, a set temperature of the reaction, or a reaction time.

20. The flow reaction method according to claim 12, wherein the reaction result is any one of a yield of a product, a yield of a by-product, a molecular weight of the product, a molecular weight dispersity of the product, or a molar concentration of the product.

* * * * *